United States Patent
Cho et al.

(10) Patent No.: US 10,186,014 B2
(45) Date of Patent: Jan. 22, 2019

(54) INFORMATION DISPLAY METHOD AND ELECTRONIC DEVICE FOR SUPPORTING THE SAME

(71) Applicant: Samsung Electronics Co., Ltd., Suwon-si, Gyeonggi-do (KR)

(72) Inventors: Jong Keun Cho, Ansan-si (KR); Jong Chae Moon, Seoul (KR); Hyo Chan Song, Seongnam-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 4 days.

(21) Appl. No.: 14/987,122

(22) Filed: Jan. 4, 2016

(65) Prior Publication Data

US 2016/0196635 A1    Jul. 7, 2016

Related U.S. Application Data

(60) Provisional application No. 62/100,267, filed on Jan. 6, 2015, provisional application No. 62/104,319, filed on Jan. 16, 2015.

(30) Foreign Application Priority Data

Feb. 17, 2015   (KR) ........................ 10-2015-0024528

(51) Int. Cl.
*G06T 3/40* (2006.01)
*G06F 3/01* (2006.01)
(Continued)

(52) U.S. Cl.
CPC ................ *G06T 3/40* (2013.01); *A61B 5/024* (2013.01); *A61B 5/14551* (2013.01);
(Continued)

(58) Field of Classification Search
CPC ......... G06T 3/40; G06T 13/80; A61B 5/6898; A61B 5/14551; A61B 5/4809;
(Continued)

(56) References Cited

U.S. PATENT DOCUMENTS

| 7,731,656 B2 | 6/2010 | Miyajima et al. |
| 8,738,665 B2 | 5/2014 | Hunter et al. |

(Continued)

FOREIGN PATENT DOCUMENTS

| EP | 2 856 936 A1 | 4/2015 |
| JP | 2002-314649 A | 10/2002 |

(Continued)

*Primary Examiner* — Ke Xiao
*Assistant Examiner* — Kim-Thanh T Tran
(74) *Attorney, Agent, or Firm* — Jefferson IP Law, LLP

(57) ABSTRACT

An electronic device and information display method are provided. The electronic device includes a memory configured to store at least one object, a display configured to output a screen associated with the at least one object, and a processor configured to functionally connect with the memory and the display. The processor controls to display a first object, associated with collected sensing information related to a human body, among objects stored in the memory, at a size on the display and to display a second object on the first object based on the sensing information. The processor modifies a size and region of the second object and a displayed motion of the second object according to accumulated sensing information and controls to output the modified second object on the first object.

15 Claims, 19 Drawing Sheets

(51) Int. Cl.
*G06T 13/80* (2011.01)
*A61B 5/00* (2006.01)
*A61B 5/024* (2006.01)
*A61B 5/1455* (2006.01)
*G06F 19/00* (2018.01)
*A61B 5/11* (2006.01)

(52) U.S. Cl.
CPC .......... *A61B 5/4809* (2013.01); *A61B 5/6898* (2013.01); *A61B 5/743* (2013.01); *G06F 3/015* (2013.01); *G06F 19/00* (2013.01); *G06T 13/80* (2013.01); *A61B 5/1118* (2013.01)

(58) Field of Classification Search
CPC ....... A61B 5/024; A61B 5/743; A61B 5/1118; A61B 5/02; G06F 3/015; A63B 71/00
USPC .......................... 345/419, 660, 440; 600/508
See application file for complete search history.

(56) References Cited

U.S. PATENT DOCUMENTS

| | | | |
|---|---|---|---|
| 9,052,803 B2 | 6/2015 | Hunter et al. | |
| 2002/0107451 A1* | 8/2002 | Pulkkinen | A61B 5/02455 600/508 |
| 2003/0120164 A1* | 6/2003 | Nielsen | A61B 5/02055 600/513 |
| 2003/0181291 A1* | 9/2003 | Ogawa | A63B 24/00 482/8 |
| 2005/0209525 A1* | 9/2005 | Bojovic | A61B 5/04011 600/512 |
| 2006/0217598 A1 | 9/2006 | Miyajima et al. | |
| 2006/0224067 A1* | 10/2006 | Giftakis | A61B 5/0402 600/483 |
| 2013/0262527 A1 | 10/2013 | Hunter et al. | |
| 2014/0135631 A1* | 5/2014 | Brumback | A61B 5/02438 600/479 |
| 2014/0344746 A1 | 11/2014 | Hunter et al. | |
| 2014/0347366 A1 | 11/2014 | Emori et al. | |
| 2015/0099991 A1 | 4/2015 | Yamaguchi et al. | |
| 2015/0196804 A1* | 7/2015 | Koduri | G06K 9/00342 482/8 |

FOREIGN PATENT DOCUMENTS

| | | |
|---|---|---|
| JP | 2003-180665 A | 7/2003 |
| JP | 2013-146463 A | 8/2013 |
| KR | 10-2006-0000333 A | 1/2006 |
| KR | 10-2006-0058105 A | 5/2006 |
| KR | 10-2010-0081177 A | 7/2010 |

* cited by examiner

INFORMATION DISPLAY METHOD AND ELECTRONIC DEVICE FOR SUPPORTING THE SAME

CROSS-REFERENCE TO RELATED APPLICATION(S)

This application claims the benefit under 35 U.S.C. § 119(e) of a U.S. Provisional application filed on Jan. 6, 2015 in the U.S. Patent and Trademark Office and assigned Ser. No. 62/100,267, of a U.S. Provisional application filed on Jan. 16, 2015 in the U.S. Patent and Trademark Office and assigned Ser. No. 62/104,319, and under 35 U.S.C. § 119(a) of a Korean patent application filed on Feb. 17, 2015 in the Korean Intellectual Property Office and assigned Serial number 10-2015-0024528, the entire disclosure of each of which is hereby incorporated by reference.

TECHNICAL FIELD

The present disclosure relates to adaptively displaying information.

BACKGROUND

In general, each of electronic devices may store applications for supporting at least one function. Also, each of the electronic devices may store information, generated in response to executing the applications, in its memory. Also, each of the electronic devices may display the information stored in the memory on its display.

In the related art, each of electronic devices passively displays information stored in its memory irrespective to situations or intention of users in a process of displaying information. Therefore, in a process of recognizing information, visibility of users is degraded or the degree of understanding of users is lowered.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an adaptive information display method for enhancing degree of understanding of information and improving visibility for displayed information by more dynamically displaying user related information and an electronic device for supporting the same.

In accordance with an aspect of the present disclosure, an electronic device is provided. The electronic device includes a memory configured to store at least one object, a display configured to output a screen associated with the at least one object, and a processor configured to functionally connect with the memory and the display. The processor controls to display a first object, associated with collected sensing information related to a human body, among objects stored in the memory and to display a second object on the first object based on the sensing information. The processor modifies a size and region of the second object and a displayed motion of the second object according to accumulated sensing information and controls to output the modified second object on the first object.

In accordance with another aspect of the present disclosure, a method of displaying information in an electronic device is provided. The method includes displaying a first object, associated with collected sensing information related to a human body among objects stored in a memory, at a size on a display, and displaying a second object on the first object based on the sensing information. The displaying of the second object includes outputting the second object, in which a size and region of the second object corresponding to an accumulated numeric value of the sensing information are modified and in which a displayed motion of the second object is modified, on the first object.

In accordance with another aspect of the present disclosure, an electronic device is provided. The electronic device includes a local-area communication module configured to establish a local-area communication channel with an external electronic device, a memory configured to store sensing information received through the local-area communication module and at least one object to be output in connection with the sensing information, and a processor configured to control to display a first object corresponding to a first range value based on the stored sensing information. The processor controls to output at least one of a second object, corresponding to a second range value corresponding to the collected sensing information, which is displayed in a form which is gradually changed from a position in the first object or a third object corresponding to a single value in the first range value.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
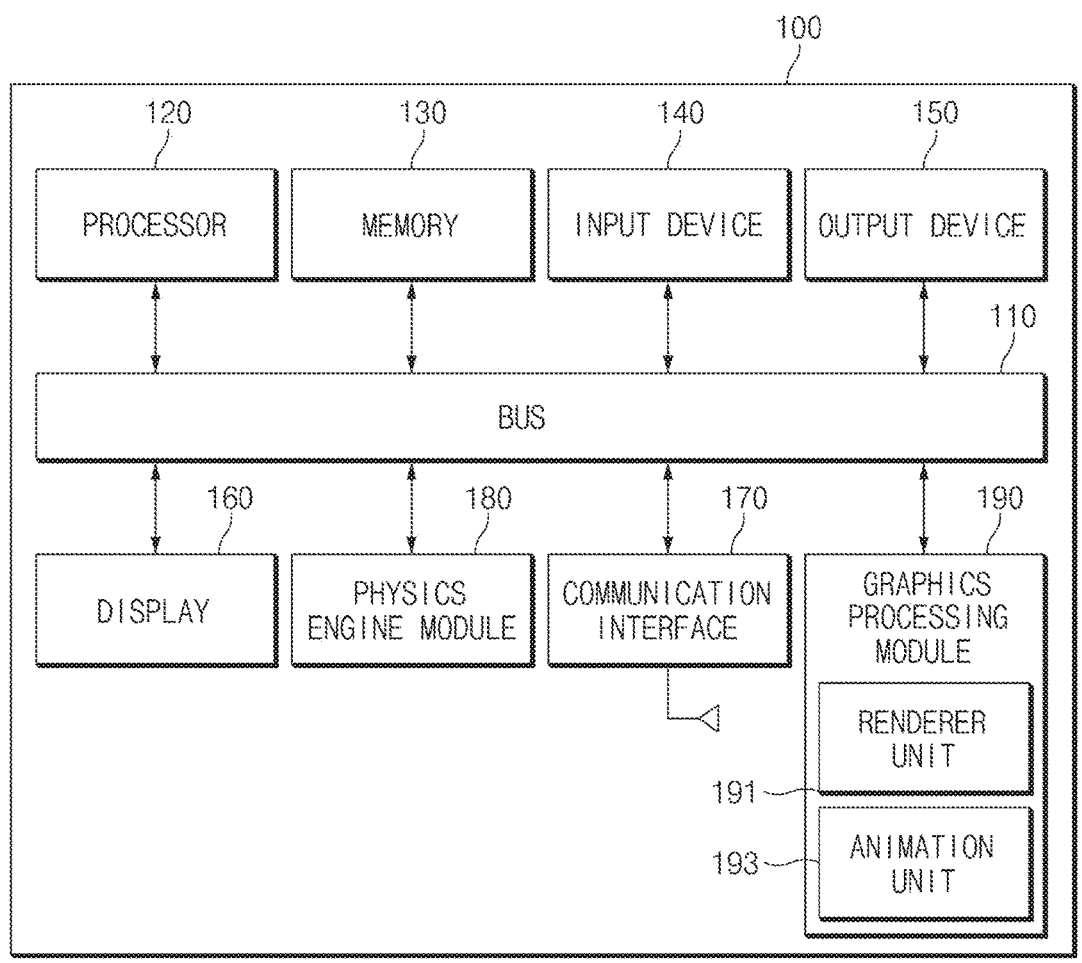
FIG. 1 is a block diagram illustrating a configuration of an electronic device according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the present disclosure, the expressions "have", "may have", "include" and "comprise", or "may include" and "may comprise" used herein indicate existence of corresponding features (e.g., elements such as numeric values, functions, operations, or components) but do not exclude presence of additional features.

In the present disclosure, the expressions "A or B", "at least one of A or/and B", or "one or more of A or/and B", and the like used herein may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The expressions such as "1st", "2nd", "first", or "second", and the like used in various embodiments of the present disclosure may refer to various elements irrespective of the order and/or priority of the corresponding elements, but do not limit the corresponding elements. The expressions may be used to distinguish one element from another element. For instance, both "a first user device" and "a second user device" indicate different user devices from each other irrespective of the order and/or priority of the corresponding elements. For example, a first component may be referred to as a second component and vice versa without departing from the scope of the present disclosure.

It will be understood that when an element (e.g., a first element) is referred to as being "(operatively or communicatively) coupled with/to" or "connected to" another element (e.g., a second element), it can be directly coupled with/to or connected to the other element or an intervening element (e.g., a third element) may be present. In contrast, when an element (e.g., a first element) is referred to as being "directly coupled with/to" or "directly connected to" another element (e.g., a second element), it should be understood that there are no intervening element (e.g., a third element).

Depending on the situation, the expression "configured to" used herein may be used as, for example, the expression "suitable for", "having the capacity to", "designed to", "adapted to", "made to", or "capable of". The term "configured to" must not be limited to mean only "specifically designed to". Instead, the expression "a device configured to" may mean that the device is "capable of" operating together with another device or other components. For example, a "processor configured to perform A, B, and C" may mean a generic-purpose processor (e.g., a central processing unit (CPU) or an application processor (AP)) which may perform corresponding operations by executing one or more software programs which stores a dedicated processor (e.g., an embedded processor) for performing a corresponding operation.

Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal detect unless expressly so defined herein in various embodiments of the present disclosure. In some cases, even if terms are terms which are defined in the specification, they may not be interpreted to exclude various embodiments of the present disclosure.

Electronic devices according to various embodiments of the present disclosure may include at least one of, for example, smart phones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group phase 1 or phase 2 (MPEG-1 or MPEG-2) audio layer III (MP3) players, mobile medical devices, cameras, or wearable devices (e.g., smart glasses, head-mounted-devices (HMDs), an electronic apparel, electronic bracelets, electronic necklaces, electronic appcessories, electronic tattoos, smart mirrors, or smart watches).

According to various embodiments of the present disclosure, the electronic devices may be smart home appliances. The smart home appliances may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, TV boxes (e.g., Samsung HomeSync™, Apple TV™, or Google TV™), game consoles (e.g., Xbox™ and PlayStation™), electronic dictionaries, electronic keys, camcorders, or electronic picture frames.

According to various embodiments of the present disclosure, the electronic devices may include at least one of various medical devices (e.g., various portable medical measurement devices (e.g., blood glucose meters, heart rate meters, blood pressure meters, or thermometers, and the like), a magnetic resonance angiography (MRA), a magnetic resonance imaging (MRI), a computed tomography (CT), scanners, or ultrasonic devices, and the like), navigation devices, global positioning system (GPS) receivers, event data recorders (EDRs), flight data recorders (FDRs), vehicle infotainment devices, electronic equipment for vessels (e.g., navigation systems, gyrocompasses, and the like), avionics, security devices, head units for vehicles, industrial or home robots, automatic teller's machines (ATMs), points of sales (POSs), or internet of things (e.g., light bulbs, various sensors, electric or gas meters, sprinkler devices, fire alarms, thermostats, street lamps, toasters, exercise equipment, hot water tanks, heaters, boilers, and the like).

According to various embodiments of the present disclosure, the electronic devices may include at least one of parts of furniture or buildings/structures, electronic boards, electronic signature receiving devices, projectors, or various measuring instruments (e.g., water meters, electricity meters, gas meters, or wave meters, and the like). The electronic devices according to various embodiments of the present disclosure may be one or more combinations of the above-mentioned devices. The electronic devices according to various embodiments of the present disclosure may be flexible electronic devices. Also, electronic devices according to various embodiments of the present disclosure are not limited to the above-mentioned devices, and may include new electronic devices according to technology development.

Hereinafter, electronic devices according to various embodiments of the present disclosure will be described with reference to the accompanying drawings. The term "user" used herein may refer to a person who uses an electronic device or may refer to a device (e.g., an artificial electronic device) that uses an electronic device.

FIG. 1 is a block diagram illustrating a configuration of an electronic device according to various embodiments of the present disclosure.

Referring to FIG. 1, an electronic device 100 according to various embodiments of the present disclosure may include a bus 110, a memory 130, an input device 140, an output device 150, a display 160, a graphics processing module 190, and a processor 120. In addition, the electronic device 100 may further include a physics engine module 180 or a communication interface 170.

The electronic device 100 may activate an application stored in the memory 130 and may operate at least one sensor. The electronic device 100 may output function information obtained through the at least one sensor to the display 160. In this operation, the electronic device 100 may analyze sensing information and state information of a user according to a predetermined condition and may dynamically output the analyzed result to suite a situation of the user. For example, the electronic device 100 may analyze sensing information (or sensor information) using various predetermined conditions and may calculate a display element in response to each of the analyzed results. In outputting the display element, the electronic device 100 may output at least one of an order of outputting the display element, an output position of the display element, a display form of the display element, or a change of the display element in a different way in response to state information of the user.

The bus 110 may transmit a signal between the components (e.g., the processor 120 to the graphics processing module 190). For example, the bus 110 may transmit sensing information collected by at least one sensor included in the input device 140 to the processor 120. The processor 120 may transmit the sensing information and user information to the graphics processing module 190 through the bus 110.

The memory 130 may include a volatile memory and/or a non-volatile memory. The memory 130 may store, for example, instructions or data associated with at least another component of the electronic device 100. According to an embodiment of the present disclosure, the memory 130 may store software and/or a program. The program may include a kernel, a middleware, an application interface (e.g., an application programming interface), or an application. At least a part of the kernel, the middleware, or the application interface may be referred to as an operating system (OS). The above-mentioned memory 130 may store sensing information collected by a sensor and user information entered by the user. The user information may include information (e.g., health, age, height, weight, biometric pattern information such as a blood pressure or a heart rate, and the like) generated through previously collected sensing information.

The input device 140 may perform an operation of receiving information entered by the user of the electronic device 100 or sensing information sensed through a sensor. The input device 140 may receive information input by an input operation (e.g., an operation of pushing a touch sensor, a button, and a key and an operation of writing with a stylus pen). According to an embodiment of the present disclosure, input contents collected by the input device 140 may include input information corresponding to managing a health care goal (e.g., one or more of an exercise level, a loss in weight, and the number of times of exercises for each exercise type) the user wants to achieve, a schedule, a telephone number, and the like.

According to an embodiment of the present disclosure, the input device 140 may sense an input signal (e.g., an input position, an input gesture, handwriting information, or a button input) through a touch sensor, a key input sensor, or a stylus pen. According to an embodiment of the present disclosure, the input device 140 may sense an impact, a vibration, a knock operation, and the like through an impact sensor and a vibration sensor (e.g., an acceleration sensor, a microphone, a pressure sensor). According to various embodiments of the present disclosure, the input device 140 may recognize a signal, for example, a connection sensing signal with a wired and wireless device.

The above-mentioned input device 140 may include at least one sensor for measuring a state of the electronic device 100, a state of the user, or a state of a surrounding environment associated with him or her. For example, the input device 140 may include at least one of a motion sensor, an environment sensor, a position sensor, or a biometric information sensor. The motion sensor may sense one or more of motion, a pose, or an orientation of the electronic device 100 or the user. The motion sensor may include at least one of an inertial sensor, a gyroscope/accelerometer, a proximity sensor, a gyroscope sensor, a magnetic sensor, an optical sensor, a red, green, blue (RGB) camera, an infrared (IR) camera, a Kinect sensor, a pressure sensor, a directional radio signal detector, an IR light emitting diode (LED), or a touch sensor. The processor 120 may sense a pose or motion of the electronic device 100 using the motion sensor and may determine an orientation of the display 160 of the electronic device 100. The processor 120 may determine an alignment orientation (e.g., a horizontal mode/vertical mode and a portrait/landscape mode) of time information to be displayed on the display 160 and may display the determined time information.

The environment sensor may measure an environment state around the electronic device 100 or the user. The environment sensor may include at least one of an illumination sensor, a gas sensor, a fine dust sensor, an atmospheric pressure sensor, a hygrometer, a thermometer, an ultraviolet (UV) sensor, a microphone, a radioactivity meter, an ozone meter, or a time sensor. The position sensor may include at least one of a GPS/global navigation satellite system (GNSS) sensor, a radio positioning sensor (e.g., one or more of a cell-identification (ID) sensor, a time of arrival (ToA) sensor, a time difference of arrival (TDoA) sensor, and an angle of arrival (AOA) sensor) based on wireless communication, or an indoor positioning sensor (e.g., a Wi-Fi fingerprint sensor, a near field communication (NFC) sensor, a radio frequency ID (RFID) sensor, a pedometer, a camera, an image marker reader, an image code reader, an IR sensor, an ultrasonic sensor, an ultra wide band (UWB) sensor) to determine a location of the electronic device 100 or the user. The position sensor may include a barometer to sense an altitude or a change of an altitude.

The biometer information sensor for measuring a health condition or an emotional state of the user may include at least one of a pedometer, a blood pressure meter, a blood glucose meter, a photoplethysmography (PPG) sensor, an electrocardiogram (ECG) sensor, an electromyography (EMG) sensor, an electroencephalogram (EEG) sensor, a blood volume pulse (BVP) sensor, a pulse oximeter oxygen saturation ($SpO_2$) sensor, a galvanic skin response (GSR) sensor, a skin conductivity (SC) sensor, a body fat analyzer, a body temperature sensor, a skin temperature sensor, a peak flow meter, or a gas sensor. The biometric information sensor may include at least one of an iris sensor, a face recognizer, a hand shape recognizer, a hand blood vessel recognizer, a voice recognizer, a handwritten signature recognizer, a camera, an IR camera, a touch sensor, or a microphone, each of which recognizes a biometric characteristics for each person.

The biometric information sensor may collect raw data (e.g., a biometric signal) which includes sensing information associated with at least one of, for example, a blood pressure, a blood flow, a heart rate (e.g., a heart rate monitor (HRM) and heart rate variability (HRV)), a body temperature, a breathing rate, oxygen saturation, a cardiopulmonary sound, a blood glucose, a waist size, height, weight, a body fat, an amount of calorie consumed, a brainwave, a voice, skin resistance, EMG, ECG, a gait, an ultrasonic image, a sleeping state, a look (face), pupil dilatation, or eye blinking.

The processor 120 may extract biometric characteristic information by analyzing the at least one sensing information, collected by the biometric information sensor, separately or by combining the at least one sensing information. For example, the processor 120 may analyze a pulse wave signal obtained through an HRV sensor to obtain primary biometric characteristic information such as an average heart rate and a heart rate distribution chart. Also, the processor 120 may process the collected biometric characteristic information to obtain secondary biometric characteristic information such as a stress state and a blood vessel aging degree, which is determined according to a complex factor.

The processor 120 may output a user biometric signal collected by the biometric information sensor. Alternatively, the processor 120 may output biometric characteristic information obtained by analyzing a biometric signal. The above-mentioned processor 120 may include a processor (or a microcomputer and the like) independently configured to operate at least one sensor. A device including the biometric information sensor may be, for example, a portable phone in which an ECG sensor is embedded, a watch in which a PPG sensor is embedded, and the like. A biometric information sensor, a sensor hub, or the processor 120 included in the electronic device 100 may analyze and operate biometric characteristic information.

According to various embodiments of the present disclosure, the electronic device 100 in which a sensor is embedded may transmit a biometric signal to a remote device (e.g., a wearable device, an accessory device, a smartphone, a home appliance, and the like) or a server device through a wired or wireless network. Also, a processor of the remote device or the server device which receives the biometric signal may process the biometric signal to generate biometric characteristic information.

According to various embodiments of the present disclosure, a device in which a sensor is embedded may generate primary biometric characteristic information and may transmit the generated primary biometric characteristic information to the remote device or the server device. The remote device or the server device may generate secondary biometric characteristic information according to the received primary biometric characteristic information. The biometric characteristic information may be displayed on at least one of the electronic device 100 or the remote device or server device.

According to various embodiments of the present disclosure, a plurality of sensors may be operated in a complex way. For example, an acceleration sensor may simultaneously measure motion of the user and the number of steps of the user. In an embodiment of the present disclosure, a PPG sensor may be used as a biometric information sensor which senses biometric information such as a heart rate and stress and may be used as a proximity sensor according to the quantity of received light. In an embodiment of the present disclosure, an ECG sensor may recognize an emotion, a heart rate, and HRV through ECG analysis and may be used for authenticating the user.

In an embodiment of the present disclosure, a sensor may be in an always-on state in a state where the electronic device 100 is powered on. In an embodiment of the present disclosure, a sensor may be driven according to an input (e.g., a key input, a button input, a graphical user interface (GUI) input, gesture recognition) of the user. According to various embodiments of the present disclosure, the sensor may be embedded in the electronic device 100, and may be embedded in another electronic device or may be installed in an external environment (e.g., the interior of a building, the exterior of a building, a predetermined building, a base station, and the like).

The output device 150 may provide information such that the user may recognize contents processed by the graphics processing module 190. For example, the output device 150 may include the display 160, an audio device, and a haptic device of the electronic device 100. The output device 150 may provide output information (e.g., an animation, an audio, a voice, tactile feedback, and force feedback) to the user through an image, a sound, and a vibration.

The display 160 may include, for example, a liquid crystal display (LCD), an LED display, an organic LED (OLED) display, a microelectromechanical systems (MEMS) display, or an electronic paper display. The display 160 may display, for example, various contents (e.g., text, images, videos, icons, or symbols, and the like) to the user. The display 160 may include a touch screen, and may receive, for example, a touch, gesture, proximity, or a hovering input using an electronic pen or a part of a body of the user.

The graphics processing module 190 may include at least one of a renderer unit 191 or an animation unit 193. All of the renderer unit 191 and the animation unit 193 may be included in the processor 120 or may be included in one or more separate processors.

The renderer unit 191 may provide its output to the output device 150. To display a generated three-dimensional (3D) graphic on the display 160, the renderer unit 191 may convert the 3D graphic into a two-dimensional (2D) graphic to suite attributes (e.g., a resolution, a refresh rate, a color model, and the like) of the display 160. Alternatively, the renderer unit 191 may generate only a region to be displayed on the display 160 from an original image and may transmit the generated region to the output device 150 (e.g., a display buffer).

The animation unit 193 may be responsible for a function for providing an effect to an object provided to the output device 150. According to an embodiment of the present disclosure, the animation unit 193 may generate a change rate, a change range, a change speed, a change effect, and the like of a UI for providing information corresponding to a statistical data calculation value, for example, an analyzed value (e.g., a maximum value, a minimum value, an average value, a median value, frequency, dispersion, a standard deviation, and the like) of sensing information measured by the input device 140.

According to an embodiment of the present disclosure, the animation unit 193 may provide an effect to a specific object included in a UI of the user provided to the output device 150 to have the same ratio of the left to right of the specific object or such that the left and right of the specific object is changed to a constant form. The specific object included in the UI of the user may be a pie-chart, a bar graph, a progress bar, and the like.

According to an embodiment of the present disclosure, the animation unit 193 may calculate attributes for object modification. The attributes for object modification may include at least one or more of position attributes (e.g., a top, a left, and a bottom), size attributes (e.g., width and height), box attributes (e.g., a margin and padding), border attributes (e.g., a border-width, a border-radius, and a border-color), color attributes (e.g., a color and a background-color), transparency attributes (e.g., opacity), or transform attributes (e.g., transform).

According to an embodiment of the present disclosure, the object modification may include at least one or more of image modification for adjusting pixels and transparency on a progress bar/circuit display region to be displayed on the display 160, image combination for synthesizing pixels of an indicator portion and a progress bar/circuit portion, which are overlapped with each other on the entire progress, according to a minimum value and a maximum value of input data, or masking for performing different calculation for each region on an image.

The processor 120 may include, for example, at least one processor. The at least one processor may include one or more of a CPU, an AP, and a communication processor (CP). The processor 120 may perform, for example, calculation or data processing about control and/or communication of at least another component of the electronic device 100.

The processor 120 may control a function of the electronic device 100 according to a user input or sensing information which is received in the input device 140. For example, to display information, associated with a state of the electronic device 100, a state of the user, or a state of a surrounding environment associated with the electronic device 100 or the user, to the user, the processor 120 may process calculation associated with information (e.g., sensing information) received through the input device 140 or biometric characteristic information. Also, the processor 120 may store the processed result in the memory 130 and may generate output information to be displayed to the user through the output device 150 using information (e.g., user related information, user input information, and the like) stored in the memory 130.

According to an embodiment of the present disclosure, the processor 120 may perform preprocessing (e.g., one or more of de-noising, segmentation, signal standardization, and feature extraction) of a motion signal or a biometric signal received through a motion sensor a biometric information sensor. The processor 120 may recognize a physical condition, an emotional state, a motion type or an exercise level of the user through signal analysis (e.g. one or more of artificial intelligence, a decision tree, pattern recognition, and user activity recognition).

The physics engine module 180 may calculate a physical characteristic in connection with the graphics processing module 190. According to an embodiment of the present disclosure, the physics engine module 180 may interwork with the animation unit 193. According to an embodiment of the present disclosure, the physics engine module 180 may be included in the graphics processing module 190. The physics engine module 180 may perform a function of calculating physics computation according to a movement path of an object, when the object is provided on a screen of the electronic device 100. The physics computation may include at least one or more of gravity, velocity, acceleration, a frictional force, a gravitational force, or an elastic force.

The communication interface 170 may establish, for example, the electronic device 100 and an external device. For example, the communication interface 170 may connect to a network through wireless communication or wired communication and may communicate with the external device. The wireless communication may use, for example, at least one of long term evolution (LTE), LTE-advanced (LTE-A), code division multiple access (CDMA), wideband CDMA (WCDMA), universal mobile telecommunications system (UMTS), wireless broadband (WiBro), or global system for mobile communications (GSM), and the like as a cellular communication protocol. The wired communication may include at least one of, for example, universal serial bus (USB) communication, high definition multimedia interface (HDMI) communication, recommended standard 232 (RS-232) communication, or plain old telephone service (POTS) communication, and the like. The network may include a telecommunications network, for example, at least one of a computer network (e.g., a local area network (LAN) or a wide area network (WAN)), the Internet, or a telephone network.

The communication interface 170 may establish a communication channel with an external electronic device and the like. The communication interface 170 may receive a biometric signal from the external electronic device or may transmit a biometric signal to the external electronic device, in response to control of the processor 120.

As described above, according to various embodiments of the present disclosure, the electronic device may include a memory configured to store at least one object, a display configured to output a screen associated with the object, and a processor configured to electrically connect with the memory and the display. The processor may display a first object, associated with collected sensing information related human body among objects stored in the memory, at a predetermined size on the display and may display a second object on the first object in connection with the sensing information. The processor may modify a size and region of the second object and a form of displayed motion of the second object according to accumulation of the sensing information and may control the display to output the modified second object on the first object.

According to various embodiments of the present disclosure, the processor may display a range value according to the accumulation of the values of the sensing information and may gradually change a predetermined numeric value from the predetermined numeric value to become the range value.

According to various embodiments of the present disclosure, the processor may change the numeric value and may display a start value and an end value of the range value. The processor may adjust a display change speed of the numeric value such that a change of a numeric value which reaches the start value of the range value and a change of a numeric value which reaches the end value of the range value are actually completed at the same time.

According to various embodiments of the present disclosure, the processor may convert the sensing information into a constant numeric value and may modify and display the second object while mapping the numeric value to the second object.

As described above, according to various embodiments of the present disclosure, the electronic device may include a memory configured to store at least one object and a processor configured to control a display to display a first object corresponding to a region of a predetermined size associated with collected sensing information among objects stored in the memory and to display a second object, corresponding to a region of a predetermined size, on the first object in connection with the sensing information. The processor may control a size and region of the second object, displayed on the first object, and a form of motion of the second object in a different way in response to the sensing information.

According to various embodiments of the present disclosure, the processor may control the display to display a third object, corresponding to a predetermined representative value obtained from the sensing information, on the first object or the second object.

According to various embodiments of the present disclosure, the processor may control the display to display a representative value corresponding to the third object on a region adjacent to a position where the third object is displayed.

According to various embodiments of the present disclosure, the processor may control the displaying and the modifying and displaying of the second object relative to a position on which the third object will be displayed.

According to various embodiments of the present disclosure, the processor may adjust a display speed of a partially modified region of the second object such that a time when the modifying and displaying of the second object is completed relative to the third object.

According to various embodiments of the present disclosure, the processor may control the display to display a range value of sensing information associated with the first object on a region adjacent to the first object or may control the display to display a range value of sensing information associated with the second object on a region adjacent to the second object.

According to various embodiments of the present disclosure, the processor may gradually change a predetermined value from the predetermined value to become the range value in the process of displaying the range value of the sensing information.

According to various embodiments of the present disclosure, the processor may adjust a display change speed of the range value such that the displaying of a start value of the range value and the displaying of an end value of the range value are completed at the same time.

According to various embodiments of the present disclosure, the processor may collect physical characteristic information associated with a state of the electronic device or a state of a human body which provides the sensing information.

According to various embodiments of the present disclosure, the processor may modify a display state of at least one of the first object, the second object, or a third object according to the physical characteristic information.

As described above, according to various embodiments of the present disclosure, the electronic device may include a local-area communication module configured to establish a local-area communication channel with an external electronic device (e.g., a wearable electronic device which may collect and transmit predetermined sensing information), a memory configured to store sensing information received through the local-area communication module and at least one object to be output in connection with the sensing information, and a processor configured to control a display to display a first object corresponding to a predetermined first range value in connection with the stored sensing information. The processor may output at least one of a second object, corresponding to a second range value corresponding to the collected sensing information, which is displayed as a form which is gradually changed from a predetermined position in the first object or a third object corresponding to a single value in the first range value.

Figure 2:
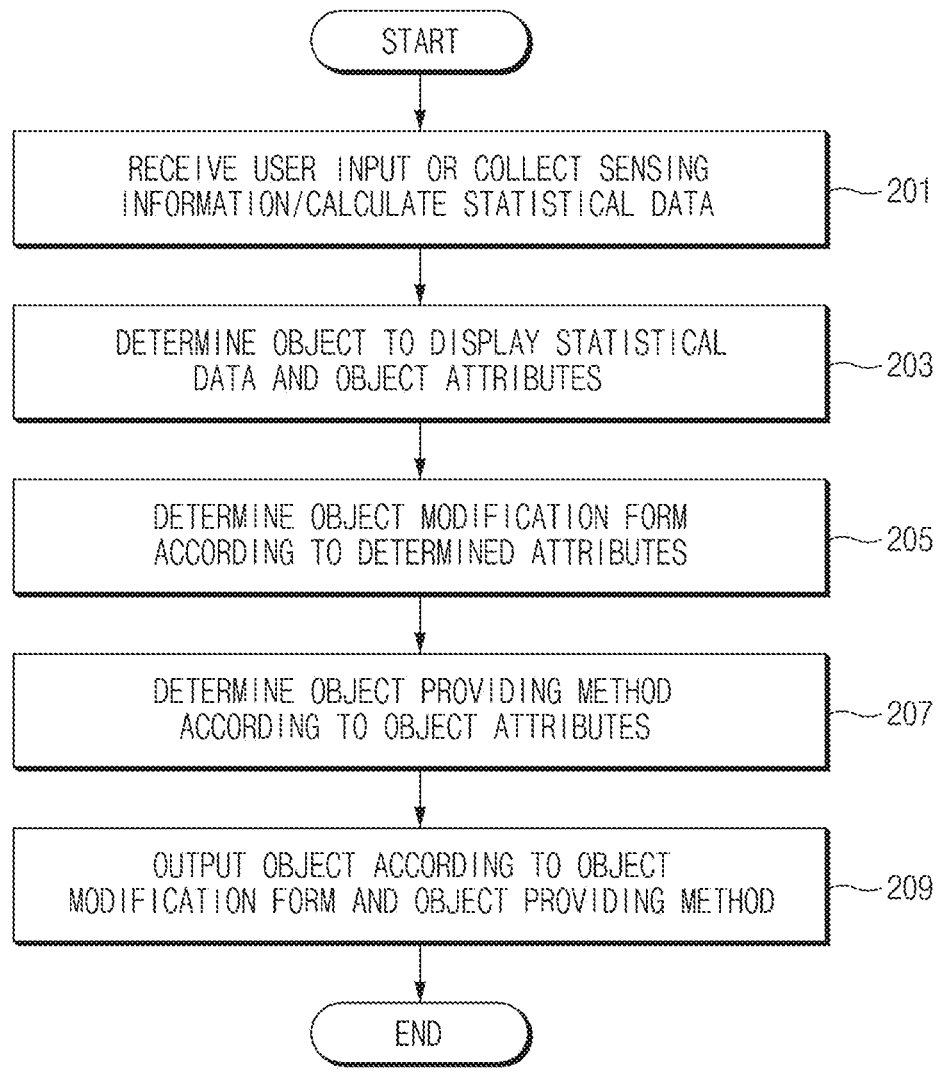
FIG. 2 is a flowchart illustrating an operation method of an electronic device according to various embodiments of the present disclosure.

FIG. 2 is a flowchart illustrating an operation method of an electronic device according to various embodiments of the present disclosure.

Referring to FIG. 2, in the operation method of the electronic device, in operation 201, an electronic device 100 of FIG. 1 may receive a user input or may collect sensing information, and may calculate statistical data. According to an embodiment of the present disclosure, the electronic device 100 may collect user state information, including a situation around the electronic device 100, through various sensors. The user state information may include an input operation (e.g., a goal the user wants to achieve or schedule information of the user, and the like) for using the electronic device 100. For example, the user state information may include information about motion, an exercise, emotion, and a physical condition of the user and situation information around the user, such as a position, a surrounding noise level, weather, temperature and humidity, altitude, and the like of the user. According to an embodiment of the present disclosure, the user state information may include a statistic (e.g., at least one of a maximum value, a minimum value, a standard deviation, an average value, a representative value, or a median value) obtained through statistical processing of a plurality of information sensed by sensors.

In operation 203, the electronic device 100 may determine an object to display the statistical data and object attributes (or a display modification characteristic of the object). According to an embodiment of the present disclosure, the electronic device 100 may select an object suitable for the user state information. The object may include at least one of a predetermined shape, a predetermined pattern, or a graphic type (e.g., a bar chart, a pie chart, a progress bar, a circular arc, a box chart, or a stem-leaf chart). According to an embodiment of the present disclosure, the object attributes may include at least one or more of position attributes (e.g., a top, a left, and a bottom), size attributes (e.g., width and height), box attributes (e.g., a margin and padding), border attributes (e.g., a border-width, a border-radius, and a border-color), color attributes (e.g., a color and a background-color), transparency attributes (e.g., opacity), or transform attributes (e.g., transform).

In operation 205, the electronic device 100 may determine an object modification form (e.g., an object region, transparency, image combination, and the like) according to the determined attributes. For example, the electronic device 100 may determine at least one of a modification rate, a change range, a change speed, or a change effect of a UI corresponding to a statistical value (e.g., a maximum value, a minimum value, an average value, a median value, and the like) of sensing information, measured by an input device 140 of FIG. 1, for being applied to the object to improve an information transmission effect to the object after selecting the object.

In operation 207, the electronic device 100 may determine an object providing method corresponding to the object attributes. According to an embodiment of the present disclosure, the electronic device 100 may determine an animation type for outputting an object. Alternatively, the electronic device 100 may determine a motion effect associated with outputting an object. Alternatively, the electronic device 100 may determine a movement route of an object. In this regard, the electronic device 100 may provide physical attributes in connection with the motion effect or the movement route. The physical attributes may include at least one or more of gravity, velocity, acceleration, a fractional force, a gravitational force, and the like obtained from sensors. In addition, the electronic device 100 may determine a form such as a sound or a vibration to be provided together according to the object attributes.

In operation 209, the electronic device 100 may output the object according to the object modification form and the object providing method. According to an embodiment of the present disclosure, if a selected object is a progress bar, the electronic device 100 may adjust a width of a left and right change by applying an object modification form of a maximum value and a minimum value and may apply an object modification form of an average value, a median value, and a representative value. A modification rate may be applied to provide an effect in which a time when a progress bar is increased for expressing a maximum value and a minimum value is spread left and right relative to a time when an average value is expressed.

If a range of a left and right change is not symmetric relative to a time when a progress bar is changed, the electronic device 100 may change a change speed of a progress bar such that a time which arrives at a predetermined left end point is identical to a time which arrives at a predetermined right end point on a display 160 of FIG. 1. For example, the electronic device 100 may adjust a left change speed and a right change speed of a progress bar according to object attributes to be applied to the progress bar.

As described above, according to various embodiments of the present disclosure, the information display method may include displaying a first object, associated with collected sensing information related human body among objects stored in the memory, at a predetermined size on the display and displaying a second object on the first object in connection with the sensing information. The displaying of the second object may include outputting a second object, in which a size and region of the second object corresponding to an accumulated numeric value of the sensing information is modified and in which a form of displayed motion of the second object is modified, on the first object.

According to various embodiments of the present disclosure, the information display method may further include gradually changing a predetermined numeric value from the predetermined numeric value to become a range value in a process of displaying the range value of the sensing information with a numeral.

According to various embodiments of the present disclosure, the information display method may further include adjusting and displaying a change speed of the numeric value such that a change of a numeric value corresponding to a start value of the range value and a change of a numeric value corresponding to an end value of the range value are actually completed at the same time.

As described above, according to various embodiments of the present disclosure, the information display method may include displaying a first object corresponding to a region of a predetermined size associated with collected sensing information and displaying a size and region of a second object, displayed on the first object, a form of motion of the second object in a different way in response to the sensing information.

According to various embodiments of the present disclosure, the information display method may further include displaying a third object, corresponding to a predetermined representative value obtained from the sensing information, on the first object or the second object.

According to various embodiments of the present disclosure, the information display method may further include displaying the representative value, corresponding to the third object, on a region adjacent to a position where the third object is displayed.

According to various embodiments of the present disclosure, the displaying of the size and region of the second region and the form of the motion of the second object in the different way may include displaying the second object and modifying and displaying the second object relative to a position where the third object will be displayed.

According to various embodiments of the present disclosure, the displaying of the size and region of the second region and the form of the motion of the second object in the different way may include adjusting and displaying a display speed of a partially modified region of the second object such that a time when the modifying and displaying of the second object is completed is identical relative to the third object.

According to various embodiments of the present disclosure, the information display method may include at least one of displaying a range value of sensing information, associated with the first object, on a region adjacent to the first object and displaying a range value of sensing information, associated with the second object, on a region adjacent to the second object.

According to various embodiments of the present disclosure, the information display method may further include gradually changing a predetermined value from the predetermined value to become a range value in a process of displaying the range value of the sensing information.

According to various embodiments of the present disclosure, the information display method may further include adjusting and displaying a display change speed of the range value such that displaying of a start value of the range value and displaying of an end value of the range value are completed at the same time.

According to various embodiments of the present disclosure, the information display method may further include collecting physical characteristic information associated with a state of the electronic device or a state of a human body which provides the sensing information.

According to various embodiments of the present disclosure, the information display method may further include modifying a display state of at least one of the first object, the second object, or a third object according to the physical characteristic information.

Figure 3A:
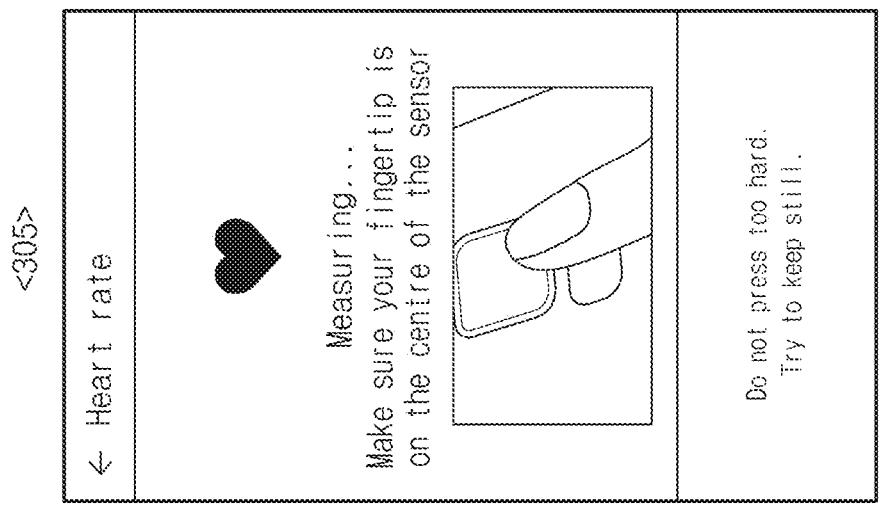
FIG. 3A is a drawing illustrating a screen interface associated with preparing for measuring biometric information according to various embodiments of the present disclosure.
Figure 3A:
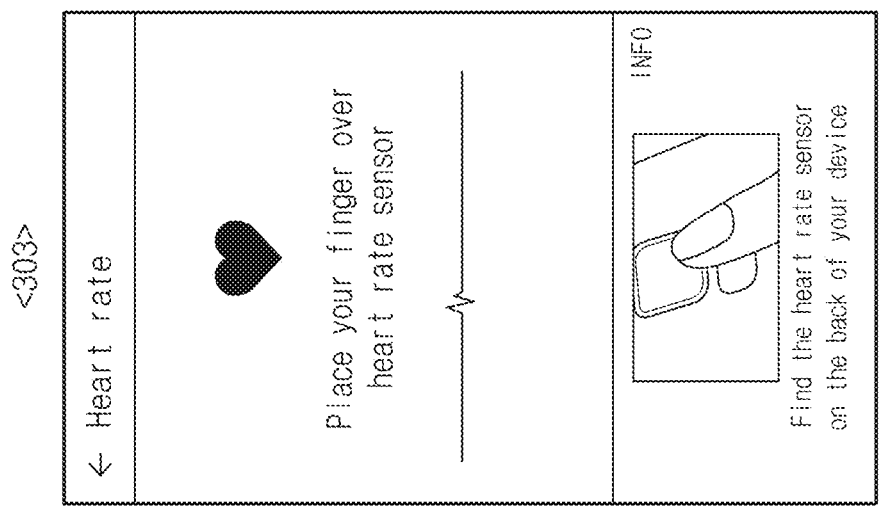
Figure 3A:
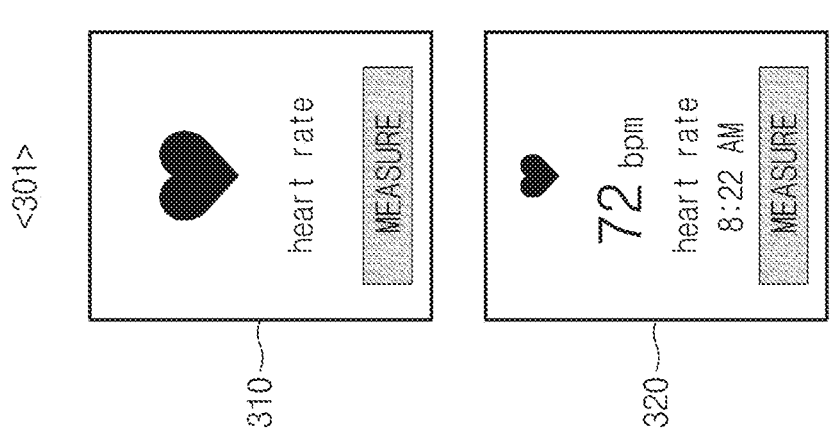

FIG. 3A is a drawing illustrating a screen interface associated with preparing for measuring biometric information according to various embodiments of the present disclosure.

Referring to FIG. 3A, state 301 may be associated with an initial screen of a biometric information display function of an electronic device 100 of FIG. 1. The electronic device 100 may activate a heartbeat application by a user input (e.g., one or more of a touch, a voice instruction, and a key input) or a certain condition (e.g., a condition in which a finger is in contact with a PPG sensor). Therefore, the electronic device 100 may display a GUI for heartbeat measurement, displayed on a display 160 of the electronic device 100, on a screen 310 of state 301. Herein, if there is previously measured heartbeat information, the electronic device 100 may display one or more of biometric information and a measurement time, which are finally measured, on a screen 320 of state 301. According to various embodiments of the present disclosure, if a user pushes a displayed virtual button (e.g., a measure GUI), the electronic device 100 may operate a biometric sensor.

If the biometric sensor is operated, the electronic device 100 may additionally perform a process of determining whether a corresponding condition is a normal measurement condition. Also, the electronic device 100 may determine a kind of the corresponding condition and may provide different guides according to a situation. For example, in state 303 or 305, the electronic device 100 may provide a guide according to a situation. According to an embodiment of the present disclosure, if it is impossible to be measured because a human body (e.g., a finger) of a user is not in normal contact with the biometric sensor or because the human body is not close to a predetermined position, in state 303, the electronic device 100 may display guide information for guiding the user to bring his or her body with the biometric sensor.

According to an embodiment of the present disclosure, the electronic device 100 may determine a biometric contact state. For example, although the human body is in contact with the biometric sensor, if it is impossible to measure the human body because the human body is close to the biometric sensor in a pressure state of a predetermined level or more, in state 305, the electronic device 100 may display guide information for guiding the user not to press the biometric sensor excessively. In connection with determining the contact state, the electronic device may operate a sensor which measures heartbeat information.

According to various embodiments of the present disclosure, the electronic device 100 may operate a PPG sensor which determines an object using one or more of an amount of a received IR optical signal reflected after an IR optical signal is irradiated to an object and a pattern of the IR optical signal. For example, when an object is closer to the PPG sensor, an amount of a received IR optical signal is more increased. Therefore, an amount of received light in case that an object is not in contact with the PPG sensor may be less decreased than that in case that the object is in contact with the PPG sensor. If strength of a signal is lower than a certain value (e.g., a maximum amount of the received light or 40% of a maximum signal level which may be measured), the electronic device 100 may determine a current state as a non-contact state or an incomplete contact state.

According to various embodiments of the present disclosure, the PPG sensor may classify a signal component into an alternating current (AC) signal component and a direct current (DC) signal component according to an amount of received light. ADC signal level may have correlation with strength of a received signal, and the AC signal component may have correlation with variance (e.g., difference between an amount of received light according to dilation of a blood vessel and an amount of received light according to constriction of a blood vessel) of the received signal. For example, if it is difficult to dilate and constrict a blood vessel because a human body is excessively close to the PPG sensor, a high DC signal level may be sensed, but a small variance amount (a change of signal strength) of the AC signal component may be sensed. Therefore, if the high DC signal level may be sensed, but if the small variance amount of the AC signal component may be sensed, the electronic device 100 may output a predetermined user guide (e.g., an image message, a voice message, haptic feedback, and the like). According to various embodiments of the present disclosure, a waveform displayed in state 303 or 305 may be a predetermined waveform image or a predetermined animation.

As described above, according to various embodiments of the present disclosure, the electronic device may include a memory configured to store at least one object and a processor configured to control a display to display a first object corresponding to a region of a predetermined size associated with collected sensing information among objects stored in the memory and to display a second object, corresponding to a region of a predetermined size, on the first object in connection with the sensing information. The processor may control the display to output contents of the second object displayed on the first object in a different way in response to a collection state (e.g., a state where sensing information may be collected or a state where sensing information may not be collected) of the sensing information.

According to various embodiments of the present disclosure, if there is history of collecting previous sensing information in a process of outputting the first object, the processor may control the display to output contents associated with the previous sensing information. If there is no previous sensing information, the processor may control the display to output predetermined contents.

Figure 3B:
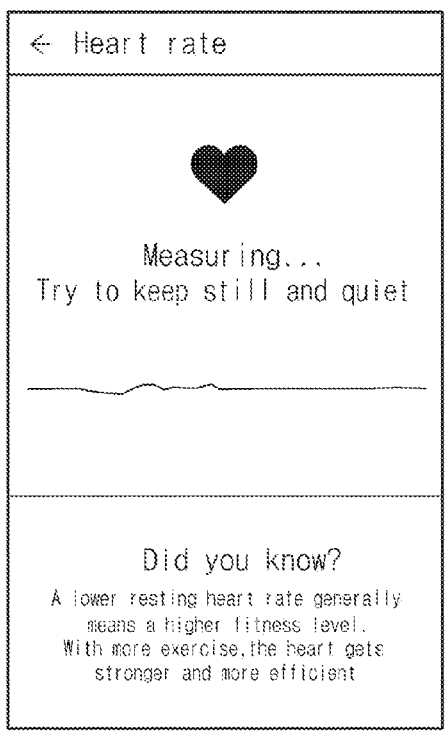
FIG. 3B is a drawing illustrating a screen interface associated with measuring biometric information according to various embodiments of the present disclosure.
Figure 3B:
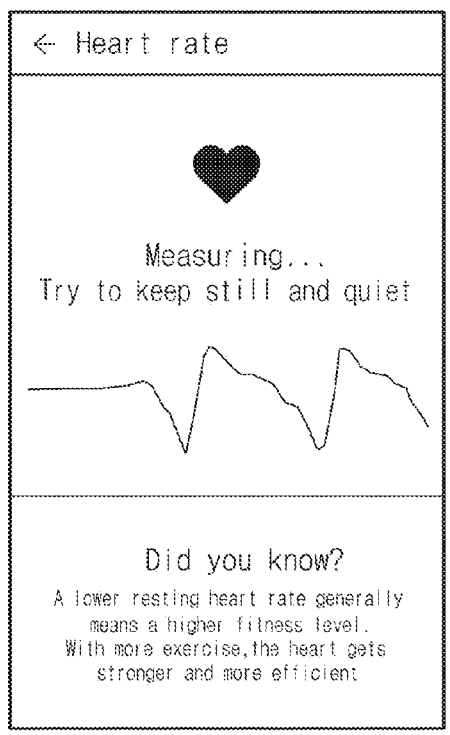
Figure 3B:
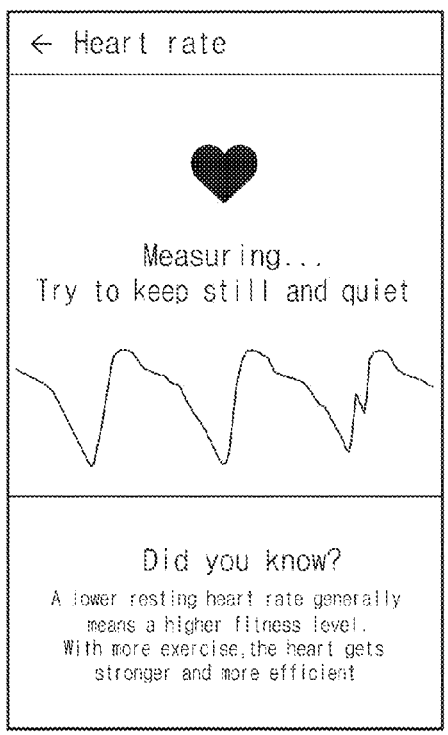
Figure 3B:
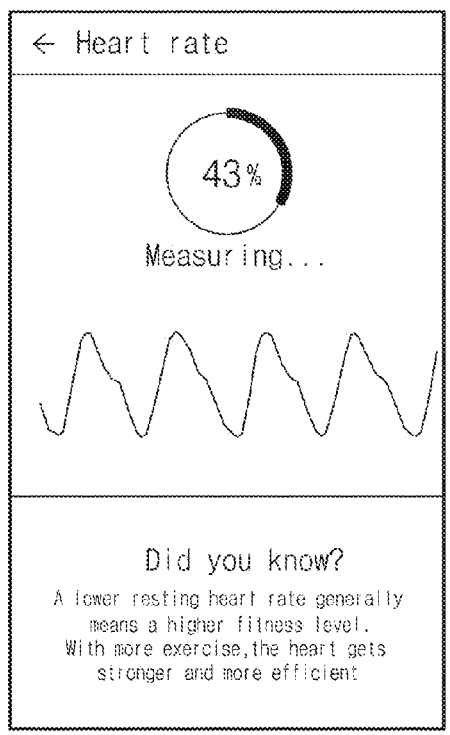

FIG. 3B is a drawing illustrating a screen interface associated with preparing for measuring biometric information according to various embodiments of the present disclosure.

Referring to FIG. 3B, an electronic device 100 of FIG. 1 may display a biometric information measurement state (e.g., measuring indication, a heart-shaped blink, and the like) together with an animation of a waveform image.

If initial measurement is started or if an abnormal biometric signal is measured, the electronic device 100 may display a screen in state 307. A biometric sensor, such as a PPG sensor or an ECG sensor, may have a need for an analysis time or a stabilization time for sensor initialization for determining a noise generation condition or a signal amplification range in sensor calibration or measurement, although a human body is normally in contact with the biometric sensor in initial measurement. Therefore, the electronic device 100 may display a predetermined waveform as an animation during a sensor initialization time. According to various embodiments of the present disclosure, if a human body is changed from a normal contact state from an abnormal contact state (e.g., if the human body is in non-contact with or in incomplete contact with the biometric sensor) while a normal waveform is measured, the electronic device 100 may display a screen in state 307. In this operation, if the human body is in the abnormal contact state during a certain time (e.g., five seconds), the electronic device 100 may detect a type of the abnormal contact state and may return the abnormal contact state to state 303 or 305 of FIG. 3A according to the detected result.

If a normal waveform is measured, in state 309 or 311, the electronic device 100 may output a waveform corresponding to the normal waveform. For example, state 309 may indicate that the measurement of the normal waveform is started after state 307 is ended. According to an embodiment of the present disclosure, the electronic device 100 may display the normal waveform by reflecting a change of the normal waveform in real time according to a change of a heartbeat, a change of an HRV value, and the like when outputting the normal waveform. Therefore, the electronic device 100 may change and display one or more of a shape or interval of a heartbeat pattern, the number of expression of the heartbeat pattern, an expression speed of the heartbeat pattern, and an expression color of the heartbeat pattern. For example, the electronic device 100 may display a waveform to which variance of a biometric signal is reflected according to the measurement of the normal waveform in state 311.

A noise of a heartbeat signal or an ECG signal sensed using PPG or ECG may be removed through a preprocessing procedure (e.g., a DC value may be compensated according to an envelope detection algorithm and acceleration-based motion detection and a high frequency and a low frequency may be removed by a high pass filter and a low pass filter, respectively). The electronic device 100 may divide a biometric signal, in which a noise is removed through a preprocessing procedure, for each period of each waveform and may normalize the magnitude of increased and decreased widths of a signal in a waveform of each period to suite a certain size region. Accordingly, the electronic device 100 may display a waveform to be displayed on a display 160 in a range of a more uniform signal level.

In state 313, the electronic device 100 may display a progress rate of processing received biometric signal information (e.g., analyzing statistics of a heart rate, calculating HRV, calculating vascular compliance, and calculating and analyzing an acceleration pulse wave) during a biometric information measurement time. In this case, a waveform may be a waveform associated with a currently measured biometric signal. Alternatively, the waveform may be patterned information obtained from a waveform, the number of expressions, and the like associated with characteristics of the entire waveform. Alternatively, the waveform may be a predetermined image which has no connection with biometric information. Therefore, the electronic device 100 may maintain dynamic information recognition, while reducing a calculation burden in a process of displaying biometric information.

As described above, according to various embodiments of the present disclosure, the electronic device may include a memory configured to store at least one object and a processor configured to control a display to display a first object corresponding to a region of a predetermined size associated with collected sensing information among objects stored in the memory and to display a second object, corresponding to a region of a predetermined size, on the first object in connection with the sensing information. The processor may control the display to output the second object in which an image form is changed in response to a change of collected sensing information.

According to various embodiments of the present disclosure, the processor may control the display to output guide information, for guiding that sensing information may not be collected or may not be collected as a predetermined form, as the second object.

According to various embodiments of the present disclosure, if sensing information is collected by a predetermined quantity, the processor may control the display to output guide information, for guiding analysis for the collected sensing information, as the second object.

According to various embodiments of the present disclosure, the processor may control the display to output a predetermined waveform as the second output while the guide information is output.

Figure 3C:
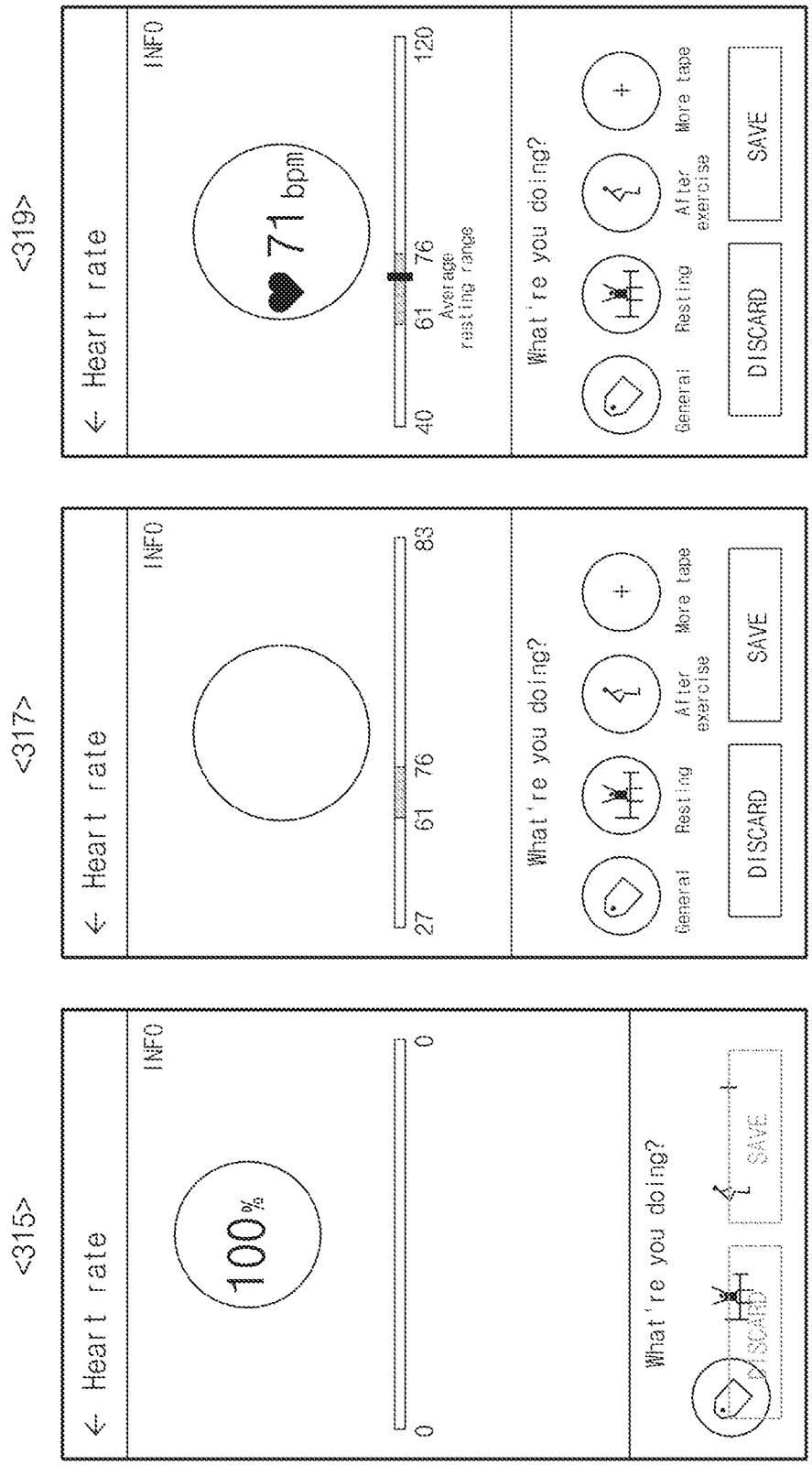
FIG. 3C is a drawing illustrating a screen interface associated with displaying the result of measuring biometric information according to various embodiments of the present disclosure.

FIG. 3C is a drawing illustrating a screen interface associated with displaying the result of measuring biometric information according to various embodiments of the present disclosure.

Referring to FIG. 3C, if measurement of normal biometric information is completed, an electronic device 100 of FIG. 1 may display a corresponding measurement result. According to an embodiment of the present disclosure, in state 315 and state 317 or 319, the electronic device 100 may process a result of measured biometric information and may display the processed information through a display 160 of FIG. 1.

According to an embodiment of the present disclosure, in state 319, the electronic device 100 may display a measurement value range (a measured maximum heart rate and a measured minimum heart rate) and an average heart rate during a measurement period of a user on a progress bar. In this operation, the electronic device 100 may display an animation effect in which one or more of a measurement value range or a progress bar are expanded left and right. The electronic device 100 may display a mark corresponding to an average heart rate on a progress bar. Also, the electronic device 100 may output numeral information corresponding to an average heart rate. Also, the electronic device 100 may display information for selecting a heart rate measurement state (e.g., a general state, after and before exercise state, and a resting state). The user may measure a heart rate after setting state selection information. According to various embodiments of the present disclosure, the electronic device 100 may automatically determine information about a current heartbeat measurement state (e.g., before exercise state, after exercise state, and a resting state) according to situation information such as motion or a schedule of the user. The selected or determined heartbeat measurement state information may be associated with measured heartbeat information and may be classified or displayed.

According to various embodiments of the present disclosure, the electronic device 100 may display proper contents together according to current biometric information or previously measured biometric information of the user. For example, referring to FIG. 3B, in states 307, 309, 311, and 313, the electronic device 100 may display predetermined guide information (e.g., information about contents that a low heart rate in a resting state is because an exercise fitness level is high) according to current or previous state information (e.g., information showing a progress in which a heart rate is reduced or a progress in which a heart rate is gradually reduced according to a previously measured history).

In connection with supporting the above-mentioned functions, the electronic device 100 may store a biometric information measurement history (e.g., a heart rate, an exercise level, an exercise time, weight, a body mass index (BMI)) of a specific user in a memory 130 of FIG. 1. The electronic device 100 may determine a progress of a biometric information measurement value or factors which have an influence on the biometric information measurement value according to the stored information. The electronic device 100 may provide various contents (e.g., the guide information) according to the determined factors. According to various embodiments of the present disclosure, the electronic device 100 may provide a proper content (e.g., exercise recommendation, food recommendation, an advertisement, a related article, health care schedule information of a user who has a similar disorder or exercise history, and the like) according to corresponding biometric information and a previous history.

As described above, according to various embodiments of the present disclosure, the electronic device may include a memory configured to store at least one object and a processor configured to control a display to display a first object corresponding to a region of a predetermined size associated with collected sensing information among objects stored in the memory and to display a second object, corresponding to a result of analyzing the sensing information, on the first object. The processor may control the display to output a displayed position, size, and color of the second object, indicated in a constant range, in a different way according to the analysis result value.

According to various embodiments of the present disclosure, the processor may control the display to output a third object, corresponding to a single value as the sensing information analysis value, on the second object.

According to various embodiments of the present disclosure, the sensing information may be heart rate information. The processor may control the display to output at least one menu item associated with a heart rate measurement environment. The processor may control the display to output guide information of other contents for a heart rate information state according to a heart rate measurement environment set in response to the selection of the menu item.

Figure 4:
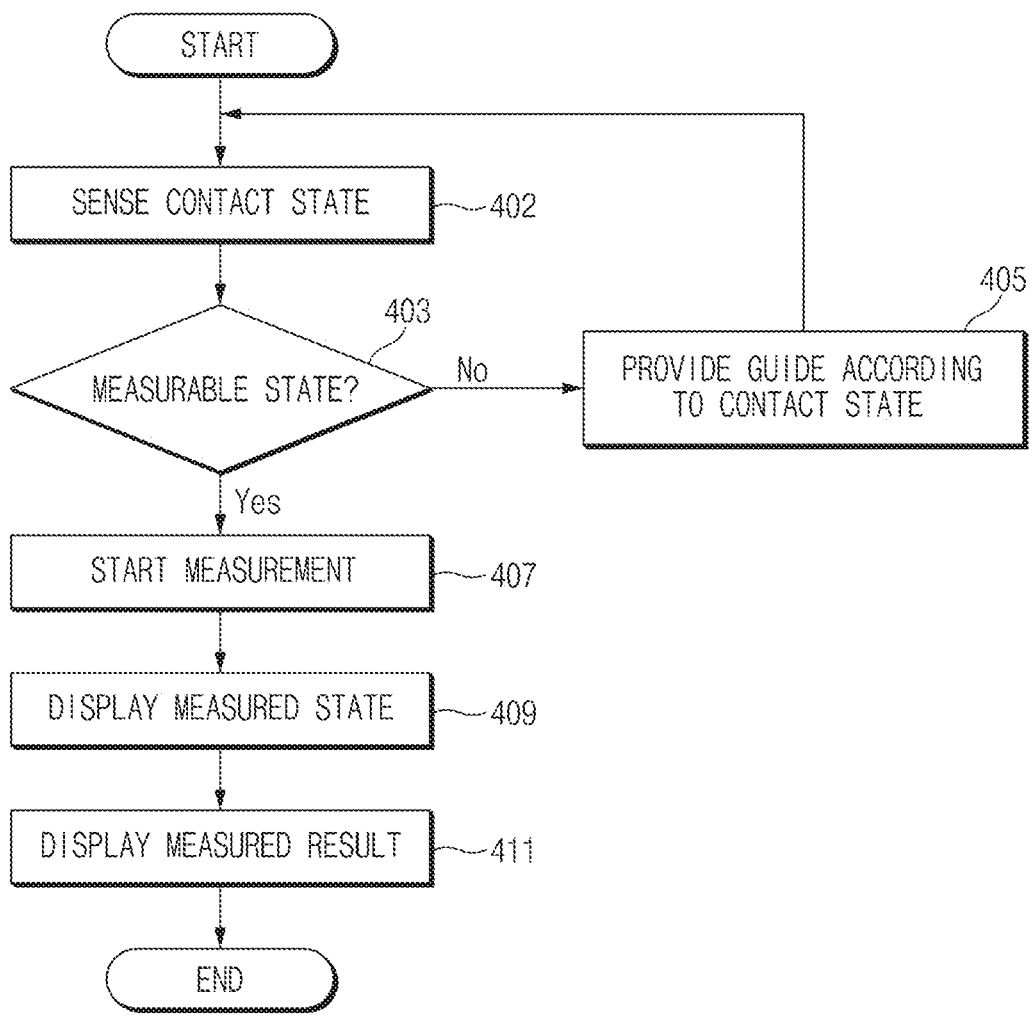
FIG. 4 is a flowchart illustrating a method for collecting biometric sensing information according to various embodiments of the present disclosure.

FIG. 4 is a flowchart illustrating a method for collecting biometric sensing information according to various embodiments of the present disclosure.

Referring to FIG. 4, in the method for collecting biometric sensing information, in operation 402, an electronic device 100 of FIG. 1 may detect a contact state (e.g., biometric contact with a PPG sensor or biometric contact with ECG electrodes). In this regard, the electronic device 100 may activate an application associated with measuring biometric information. Also, the electronic device 100 may activate a sensor associated with measuring biometric information. The electronic device 100 may detect a contact state according to sensing information collected through the sensor.

In operation 403, the electronic device 100 may verify whether a current state is a measurable state. For example, the electronic device 100 may verify whether sensing information within a predetermined range which meets a predetermined condition (e.g., a condition which maintains a state where a finger of a user is close within a constant range of a sensor or is in contact with the sensor) is collected. If the current state is a measurement impossible state (e.g., if the current state is a state where sensing information departing from a predetermined range is collected during a predetermined time), in operation 405, the electronic device 100 may provide guide information according to a contact state. For example, the electronic device 100 may output guide information for guiding the user to place his or her finger on a correct position of a sensor or guide information for guiding him or her to reduce pressure of his or her finger, which is excessively pressed.

If the current state is the measurable state (e.g., a state where sensing information of a predetermined range is collected during a predetermined time), in operation 407, the electronic device 100 may perform measurement. For example, the electronic device 100 may collect sensing information within a valid range. In operation 409, the electronic device 100 may display a measured state. For example, the electronic device 100 may output state information about whether normal sensing information (e.g., sensing information within a predetermined range) is currently collected or state information about whether abnormal sensing information (e.g., sensing information departing from the predetermined range) is currently collected. The electronic device 100 may output at least one of elapsed time information indicating whether sensing information is measured for a while or duration information indicating whether sensing information is measured for a while, or may output the entire measurement time information and the like. According to various embodiments of the present disclosure, the electronic device 100 may output a predetermined waveform in a measurement start portion. After sensing information is measured, if the sensing information is collected by predetermined amplitude, the electronic device 100 may output a real-time waveform corresponding to the corresponding sensing information.

In operation 411, the electronic device 100 may output the measured result. For example, the electronic device 100 may output at least one of collected sensing information, statistical data information of sensing information, previous history information, accumulated and calculated information, or guide information corresponding to the information. Also, the electronic device 100 may output information for selecting a measurement situation. If the measurement situation is selected, the electronic device 100 may output guide information corresponding to a corresponding state.

According to various embodiments of the present disclosure, at least one of a measurement ready operation, a measurement operation, or a measured result display operation may be performed by a wearable electronic device. Alternatively, the wearable electronic device may perform a measurement ready function, a measurement function, and a measured result transmission function. In this regard, the wearable electronic device may perform the measurement ready operation. If a measured result is collected, the wearable electronic device may transmit collected sensing information to an electronic device in which a local-area communication channel is established. Each of the wearable electronic device and the electronic device may include a local-area communication module for establishing the local-area communication channel.

Figure 5A:
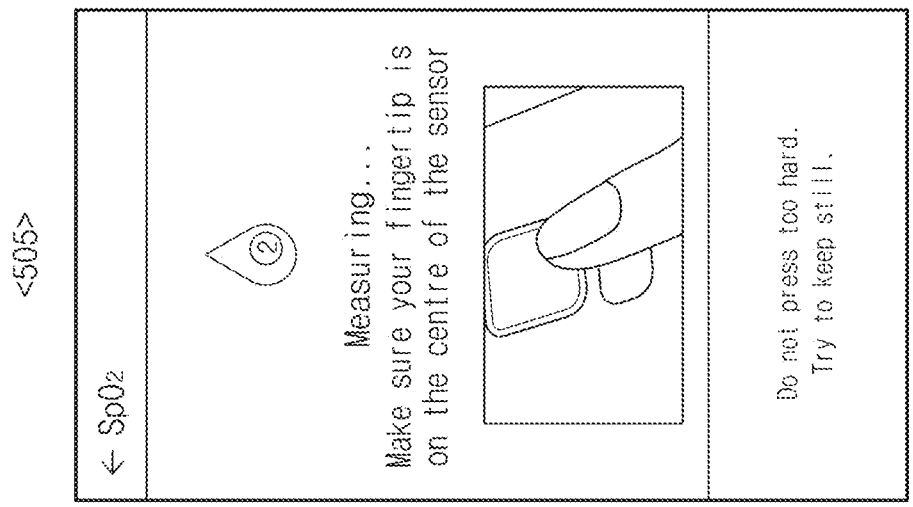
FIG. 5A is a drawing illustrating a screen interface associated with preparing for measuring pulse oximeter oxygen saturation ($SpO_2$) according to various embodiments of the present disclosure.
Figure 5A:
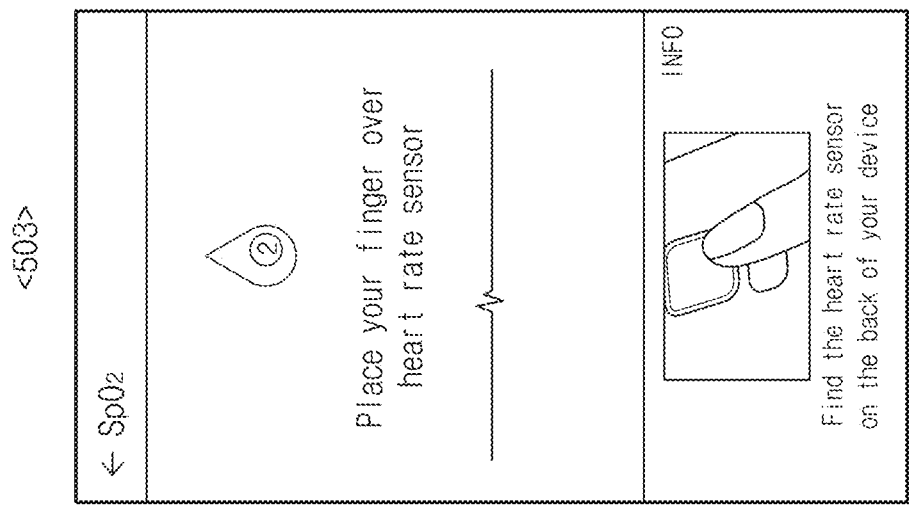
Figure 5A:
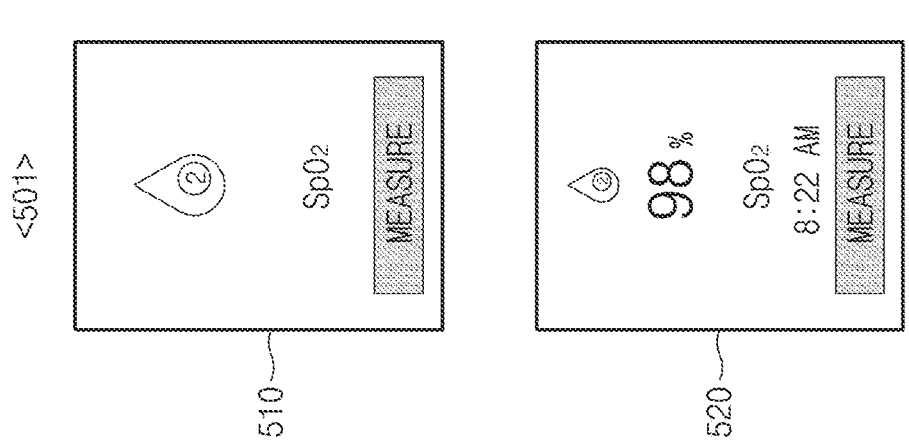

FIG. 5A is a drawing illustrating a screen interface associated with preparing for measuring $SpO_2$ according to various embodiments of the present disclosure.

Referring to FIG. 5A, in states 501, 503, and 505, an electronic device 100 of FIG. 1 may output a screen associated with preparing for measuring $SpO_2$ using a PPG sensor. If measuring $SpO_2$, the electronic device 100 may determine whether the measurement is normally performed using a sensed heartbeat signal. The electronic device 100 may generate and output a heartbeat waveform image, associated with a feature of a heartbeat signal, using the feature of the heartbeat signal.

If an event for transmitting a request for measuring $SpO_2$ occurs, the electronic device 100 may activate an application associated with measuring $SpO_2$. In this operation, the electronic device 100 may output screens 510 and 520 corresponding to activation of the application or a sensor associated with measuring $SpO_2$ in state 501. According to an embodiment of the present disclosure, if there is no previously measured history, the electronic device 100 may output the screen 510. If there is a previously measured history, the electronic device 100 may output the screen 520 associated with the previously measured history (e.g., one or more of a previously measured result or a previously measured time).

The electronic device 100 may output guide information associated with performing an operation of a user to measure $SpO_2$ in state 503 or 505. For example, the electronic device 100 may output a screen of state 503 for providing a correct finger position or may output a screen of state 505 for requesting the user to keep a predetermined pressure state.

Figure 5B:
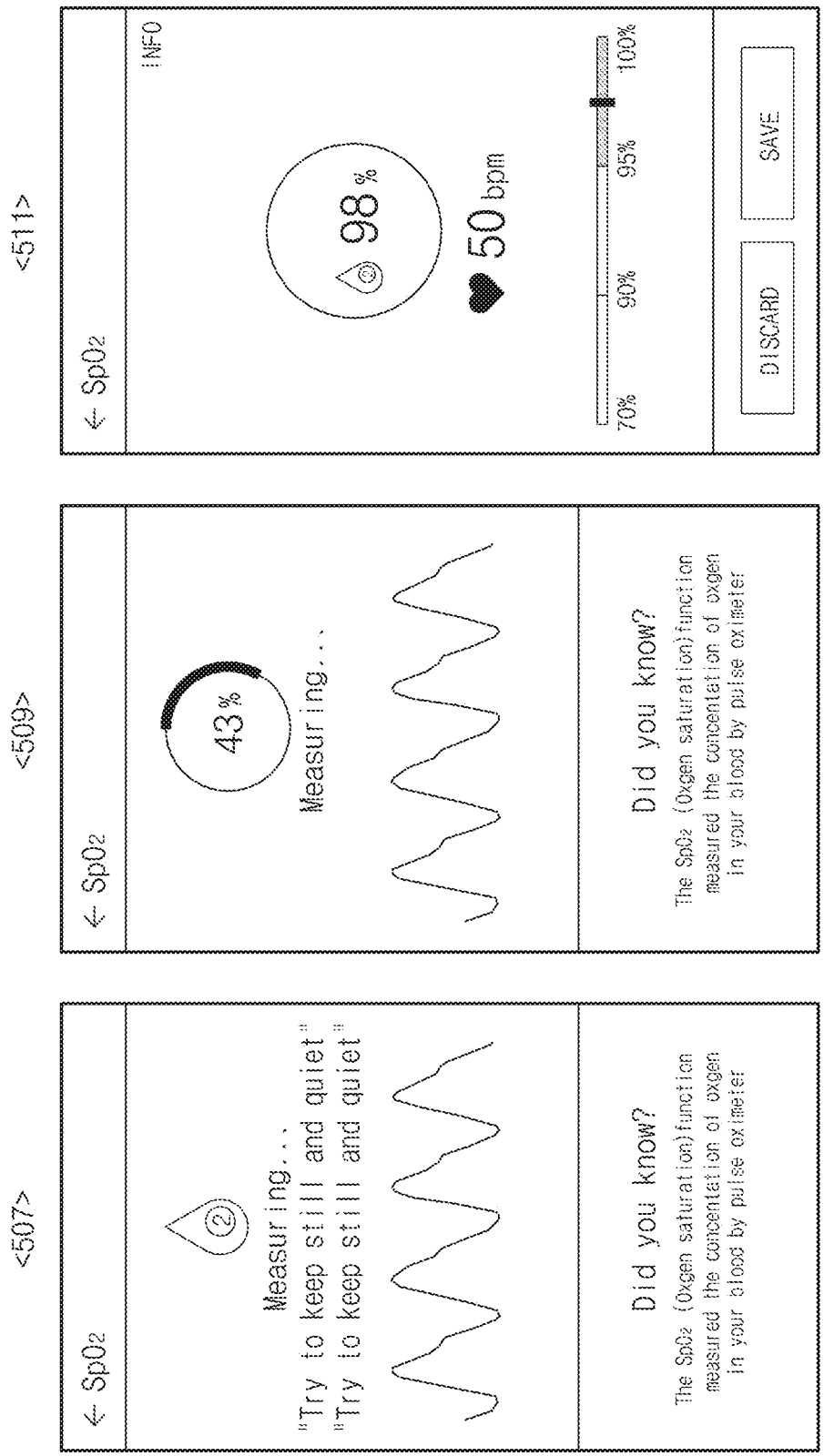
FIG. 5B is a drawing illustrating a screen interface associated with measuring SpO$_2$ and outputting the result of measuring SpO$_2$ according to various embodiments of the present disclosure.

FIG. 5B is a drawing illustrating a screen interface associated with measuring $SpO_2$ and outputting the result of measuring $SpO_2$ according to various embodiments of the present disclosure.

Referring to FIG. 5B, in state 507, 509, or 511, an electronic device 100 of FIG. 1 may display measured sensing information and result information about the measured sensing information. According to an embodiment of the present disclosure, in state 511, the electronic device 100 may display measured $SpO_2$ using a numeral and a marker on a progress bar. The progress bar may be classified as a poor region, a normal region, or a good region. The electronic device 100 may provide a support such that a user may easily recognize qualitative evaluation of a measured result by determining a position of the marker in response to a sensing information result.

Measured biometric information may be displayed in various methods. According to an embodiment of the present disclosure, the electronic device 100 may provide a selection menu for allowing the user to select a method for displaying one or more statistics associated with biometric information. For example, the selection menu may include at least one of a progress bar, a pie graph, a vertical bar graph, audio feedback, or haptic feedback.

In connection with outputting a progress bar, the electronic device 100 may calculate a first range value (e.g., a maximum value in the entire region and a minimum value in the entire region) for displaying the entire range value of the progress bar, one or more second range values (e.g., a maximum value for each region and a minimum value for each region) for displaying a range value of a partial region of the progress bar, and a representative value for displaying a representative marker according to collected sensing information.

A range and a unit of the first range value may be changed according to a biometric information value to be measured. For example, the first range value may be set to a certain range (e.g., at least one of a valid measurement range in a heart rate sensor or a range set by the user, a range by default settings of the electronic device 100, or a heart rate possible range of a person, in case of heartbeat). Alternatively, the first range value may be set according to the user or user state information (e.g., a range of maximum heartbeat information to minimum heartbeat information among previous records of a specific user, a range of a minimum heart rate to a maximum heart rate according to a set exercise goal, a range of a minimum heart rate to a maximum heart rate according to an exercise or resting state, and the like). According to various embodiments of the present disclosure, in case of a body temperature sensor or a skin temperature sensor, the first range value may include at least one of, for example, a valid measurement range, a body temperature range of a person, or a certain range. In case of a humidity sensor, the first range value may be a humidity measurement possible range (e.g., a range of 10% to 100%). In case of a blood glucose sensor, the first range value may include at least one of a valid measurement range or a glucose range of a person.

The second range value may be a value calculated according to a range of specific values extracted from two or more biometric signal information which are currently measuring or are previously measured. For example, in case of heartbeat, the second range value may include at least one of a range by a maximum heart rate and a minimum heart rate extracted from heart rate information sampled during measurement, an average±3% standard deviation range, a 95% confidence interval, a normal heartbeat range, a goal heart rate range, or a range of a $25^{th}$ percentile to a $75^{th}$ percentile. In case of the human body sensor or the skin temperature sensor, the second range value may include at least one of a maximum/minimum value range of a measured temperature or a normal body temperature range. In case of the humidity sensor, the second range value may include a maximum/minimum range of measured humidity and a reference humidity range (e.g., at least one of a maximum/minimum humidity range of day of a corresponding area through a weather center server or an average maximum and minimum humidity range determined through previously measured one or more humidity measurement histories of the electronic device 100). In case of the blood glucose sensor, the second range value may include at least one of a maximum/minimum range and a normal glucose range according to previously measured blood glucose information.

The representative value may include one or more values which may represent biometric signal information. For example, the representative value may include at least one of a single value, an average value, a median value, a 50$^{th}$ percentile, a mode, an expected value, a maximum value, a minimum value, skewness, dispersion, or standard deviation. The representative value may be obtained according to previously measured biometric information or may be obtained from a set of biometric information which is being measured.

In state 511, the electronic device 100 may display an interval (e.g., an interval where a representative value marker corresponding to a representative value is disposed) of 95% to 100% of a progress bar as an animation. For example, a bar-shaped image having a constant color may be gradually expanded and displayed relative to a representative value marker in an empty progress bar. The bar-shaped image may be gradually changed in shape from, for example, a point where the representative value marker is displayed and may be expanded in only an interval of 95% to 100%.

Figure 6A:
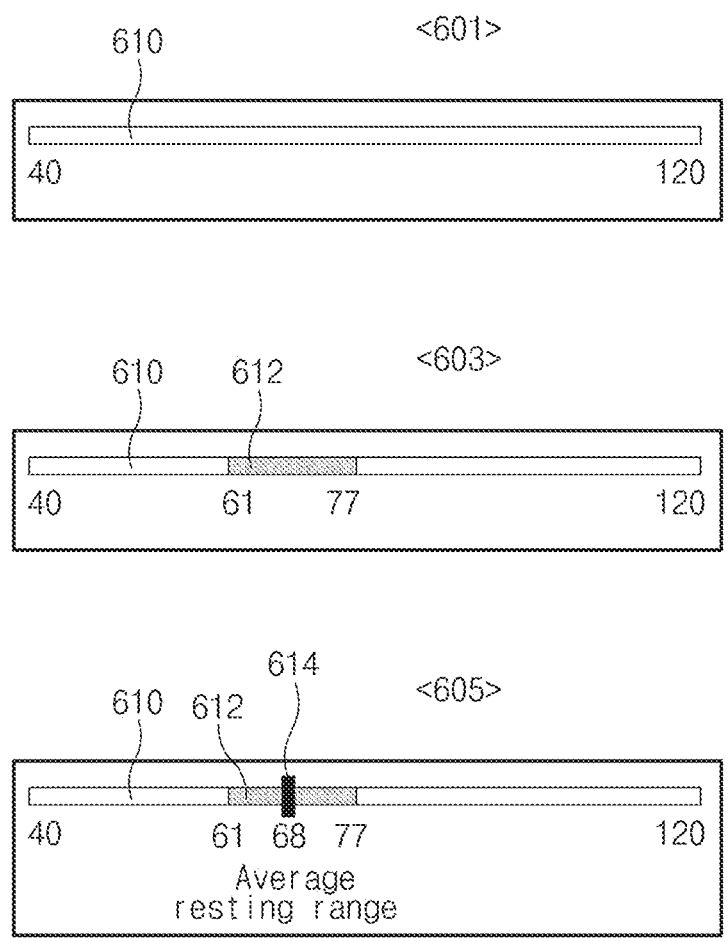
FIG. 6A is a drawing illustrating a form of displaying a progress bar according to various embodiments of the present disclosure.

FIG. 6A is a drawing illustrating a form of displaying a progress bar according to various embodiments of the present disclosure.

Referring to FIG. 6A, in displaying a progress bar, an electronic device 100 of FIG. 1 may display a variety of information according to an object to display a result of measuring biometric information. For example, in state 601, the electronic device 100 may set a first range value (e.g., a range value of 0 to 200) for displaying a progress bar after measuring heartbeat. According to an embodiment of the present disclosure, the first range value displayed on a display 160 of FIG. 1 may be determined at a time when a first object 610 corresponding to the first range value is output. For example, the first range value (e.g., the range value of 0 to 200) which is initially set may be a first range value (e.g., a range value of 40 to 120) changed according to attributes (e.g., resolution, a displayable color candidate, a supportable font size, and the like) of the display 160.

The electronic device 100 may detect a plurality of heartbeat waveforms from a heartbeat signal while measuring heartbeat. In this case, the electronic device 100 may determine a heart rate and HRV per unit time according to peak signals of the plurality of heartbeat waveforms. Therefore, the electronic device 100 may calculate various statistics for the plurality of waveforms and may determine a second range value and a representative value according to the various statistics. According to an embodiment of the present disclosure, in state 603, the electronic device 100 may output a second object 612 corresponding to a second range value which includes a minimum heart rate (e.g., 61) per unit time (e.g., one minutes) and a maximum heart rate (e.g., 77) per unit time which are detected during a heartbeat measurement interval of one time. According to an embodiment of the present disclosure, the heartbeat measurement interval of one time may include states 309 to 313 of FIG. 3B. According to an embodiment of the present disclosure, the heartbeat measurement interval of one time may be a certain time (e.g., one or more of a time several times of a unit time and the generated number of certain heartbeat P-waves). According to various embodiments of the present disclosure, the heartbeat measurement interval of one time should not need to meet the unit time. For example, the heartbeat measurement interval of one time may be obtained by estimating a heart rate per unit time according to a measured result during a time interval which is shorter than the unit time, although heartbeat of one time is measured during a time which is shorter than the unit time.

The electronic device 100 may display the first object 610 of a progress bar shape corresponding to the first range value, may display the second object 612 corresponding to the second range value, and may display a third object 614 corresponding to a representative value marker. For example, in state 605, the electronic device 100 may output the third object 614 corresponding to a representative value (e.g., an average value 68) on a constant position in the second object 612 corresponding to the second range value. In this operation, numeral information (e.g., 68) corresponding to the representative value may be displayed.

In connection with outputting the first object 610, the second object 612, and the third object 614, the electronic device 100 may determine object attributes of a progress bar to be displayed through a graphics processing module 190 of FIG. 1 using the first range value. The electronic device 100 may generate and display an object according to the determined attributes. The first object 610 corresponding to the progress bar may be displayed with a first color, a first pattern, and a first shape. The electronic device 100 may display the first object 610 having the first range value (e.g., the range value of 40 to 120) with respect to a progress bar to be displayed.

According to an embodiment of the present disclosure, the electronic device 100 may display the second object 612, corresponding to a partial region according to the second range value, on the displayed first object 610. The second object 612 may be displayed on a display 160 of FIG. 1 with a second color, a second pattern, and a second shape. For example, the second range value may be 61 to 77 and may be an interval which includes a minimum heart rate and a maximum heart rate sensed while normal heartbeat is measured.

According to an embodiment of the present disclosure, the third object 614 may be displayed together with the first object 610 or the second object 612. According to an embodiment of the present disclosure, a representative value may be displayed near the third object 614.

According to an embodiment of the present disclosure, when displaying the first object 610, the second object 612, and the third object 614, the electronic device 100 may set different object attributes (e.g., combinations of one or more of a color, a pattern, a shape, a size, a figure, a font, and transparency). According to an embodiment of the present disclosure, when displaying the first object 610, the second object 612, and the third object 614, the electronic device 100 may use different object attributes. According to an embodiment of the present disclosure, the electronic device 100 may display the first range value and the second range value on regions adjacent to related objects (e.g., the first object 610 and the second object 612) and may display a representative value on another region (e.g., in a heart region of state 319 of FIG. 3) which is not adjacent to the related objects.

As described above, in a process of outputting a result of collecting biometric information, the electronic device 100 may select an object corresponding to information (e.g., a type of biometric information) to be output and may analyze a characteristic of the information to be output. The electronic device 100 may determine attributes of the object according to the analyzed information and may determine a modification form of the object according to the determined object attributes. Also, the electronic device 100 may determine a screen effect such as an animation suitable for the modification form of the object. Therefore, the electronic device 100 may provide a support to output information of a form for being recognized by a user in response to a type of user related information, a current state, and the like.

Figure 6B:
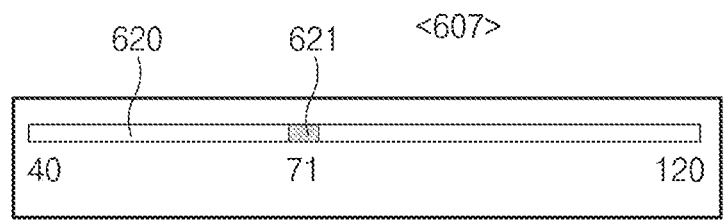
FIG. 6B is a drawing illustrating a form of displaying a progress bar according to various embodiments of the present disclosure.
Figure 6B:
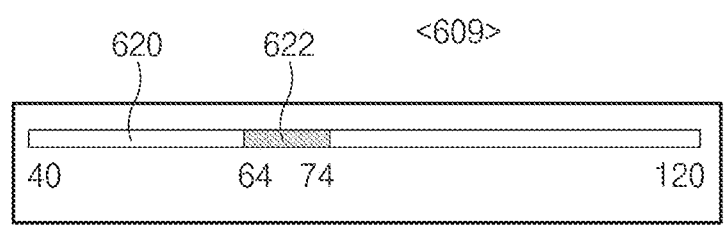
Figure 6B:
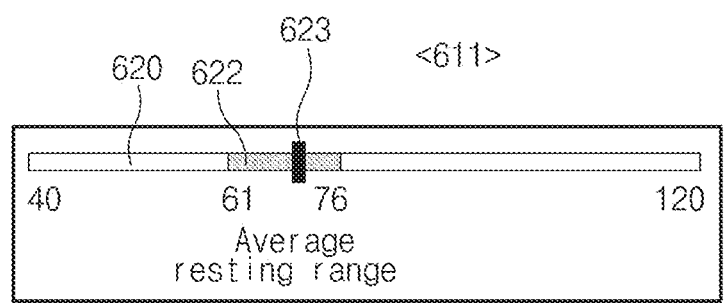

FIG. 6B is a drawing illustrating a form of displaying a progress bar according to various embodiments of the present disclosure.

Referring to FIG. 6B, in state 607, an electronic device 100 of FIG. 1 may display a 4$^{th}$ object 620 (e.g., a progress bar). In this process, the electronic device 100 may display an initial object 621 corresponding to a predetermined representative value. The representative value of the initial object 621 may be, for example, 71. Also, in state 609, the electronic device 100 may display a 5$^{th}$ object 622 corresponding to a second range value relative to the initial object 621. Also, in state 611, the electronic device 100 may control a display 160 of FIG. 1 to display a part of the 5$^{th}$ object 622 relative to a position where the initial object 621 is displayed, may gradually increase the part of the 5$^{th}$ object 622 at a size corresponding to the second range value, and may control the display 160 to display a 6$^{th}$ object 623. Herein, a first range value corresponding to the 4$^{th}$ object 620 may be a range value of 40 to 120, and the second range value corresponding to the 5$^{th}$ object 622 may be a range value of 64 to 74. A representative value corresponding to the 6$^{th}$ object 623 may be 71.

According to various embodiments of the present disclosure, the electronic device 100 may determine a position for an average value (a representative value) on the 4$^{th}$ object 620 (e.g., a progress bar) indicating the entire measurement range using statistics obtained through the measurement of biometric information. If the position of the average value is determined, the electronic device 100 may display a value corresponding to a maximum or minimum range of biometric information measured left or right relative to the determined position.

To display a maximum value or a minimum value, the electronic device 100 may process the 5$^{th}$ object 622 corresponding to a constant region of the left and right relative to the average value to be changed (e.g., an image, a color, transparency, a shadow, and the like indicating a range of a region) to the maximum value or the minimum value.

According to an embodiment of the present disclosure, a speed at which the 5$^{th}$ object 622 is filled may be determined relative to a distance from the average value to the maximum value and the minimum value. Herein, since the distance from the average value to the maximum value and the minimum value differs whenever measured, the electronic device 100 may process a speed at which the 5$^{th}$ object 622 is filled in a different way according to situations. For example, in state 605 of FIG. 6A, if a representative value is located in the center of a second object 612 (e.g., if an average value is identical to a median value), change speeds for changing an object form to the end of the second object 612 in the left and right relative to the position of the representative value may be set to be identical to each other. Accordingly, a form in which the second object 612 is changed on a third object 614 may be symmetric.

According to various embodiments of the present disclosure, if a position of a representative value (e.g., a heartbeat average value) is leaned to one side of the 5$^{th}$ object 622, speeds at which the initial object 621 is filled, which are started from a point of the initial object 621 corresponding to the representative value, may differ from each other. For example, the electronic device 100 may process the 5$^{th}$ object 622 such that the drawing of the 5$^{th}$ object 622 is ended in the actually same or similar time by differing in left and right change speeds of the 5$^{th}$ object 622 in consideration of left and right rates. Therefore, the electronic device 100 may process a form in which a part of the 5$^{th}$ object 622 is output and a form in which the other part of the 5$^{th}$ object 622 is output in a different way relative to the initial object 621. In this regard, the electronic device 100 may perform calculation (e.g., calculation of a speed processed in an animation unit 193 of a graphics processing module 190 of FIG. 1) associated with outputting the 5$^{th}$ object.

According to various embodiments of the present disclosure, attributes (e.g., a color, a pattern, transparency, and a shadow) of the initial object 621 may be identical to those of the 5$^{th}$ object 622 or the 6$^{th}$ object 623.

According to various embodiments of the present disclosure, the electronic device 100 may apply physical quantities obtained through a physics engine module 180 of FIG. 1 when displaying the second object 612 or the 5$^{th}$ object 622. For example, the electronic device 100 may apply a fluid pressure, an air pressure, or a magnetic force for each of left and right directions of the second object 612 or the 5$^{th}$ object 622 in a different way relative to the initial object 621 (or the third object 614) using the obtained physical quantities. Therefore, the electronic device 100 may process portions of the second object 612 or the 5$^{th}$ object 622 to differ in a speed or a form in which the portions of the second object 612 or the 5$^{th}$ object 622 are displayed.

Figure 6C:
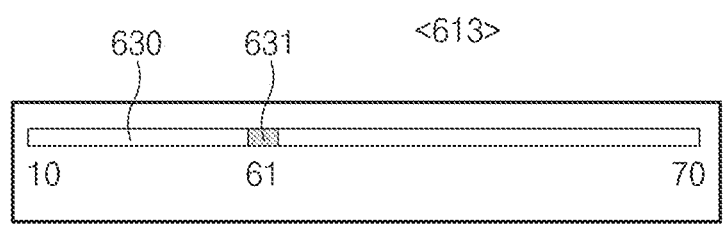
FIG. 6C is a drawing illustrating a form of displaying a progress bar according to various embodiments of the present disclosure.
Figure 6C:
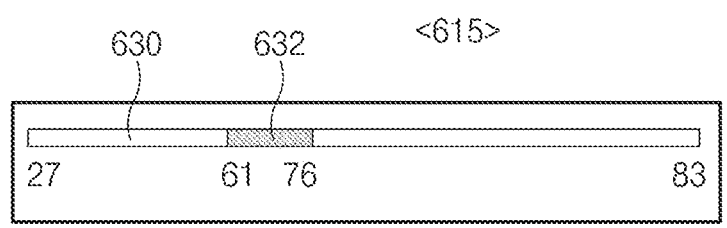
Figure 6C:
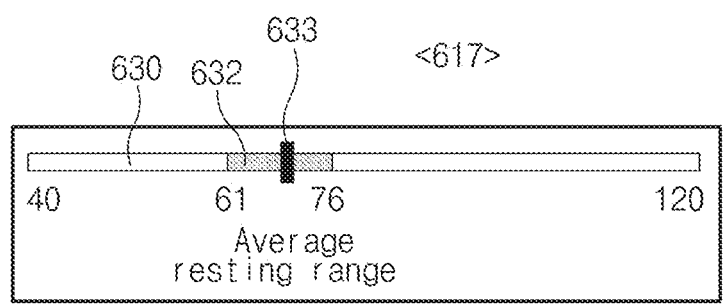

FIG. 6C is a drawing illustrating a form of displaying a progress bar according to various embodiments of the present disclosure.

Referring to FIG. 6C, in state 613, an electronic device 100 of FIG. 1 may display a 7$^{th}$ object 630 (e.g., a progress bar) and may output a start object 631 corresponding to a second range value initially obtained at a constant point. In state 615, the electronic device 100 may display an 8$^{th}$ object 632 (a partial region) corresponding to a changed second range value on the 7$^{th}$ object 630. In this case, the electronic device 100 may first display a part of the 8$^{th}$ object 632 and may output the 8$^{th}$ object 632 in a form which is changed in response to an elapsed time. In state 617, the electronic device 100 may output a 9$^{th}$ object 633 on a constant point of the 8$^{th}$ object 632.

According to various embodiments of the present disclosure, a first range value may be set to an initial value in a start point of measuring biometric information and may be continuously changed according to an update situation of objects. For example, in states 613 to 617, a start value of first range values of the 7$^{th}$ object 630 may be 10, and the start value may be changed to 27 and 40 by being gradually changed. Alternatively, the first range value may be finally displayed as 40 by being increased by a constant unit (e.g., 1 or 2, and the like). Similarly, an end value among the first range values of the 7$^{th}$ object 630 may be initially 70 and may be changed to 83 and 120 by being gradually changed. The end value may be finally displayed as 120 by being increased by a constant unit (e.g., 3 or 4, and the like).

According to an embodiment of the present disclosure, if a size of the 8$^{th}$ object 632, displayed on a display 160 of FIG. 1, corresponding to the second range value is less than or equal to a certain size, the electronic device 100 may display only one of a minimum value or a maximum value of a region in connection with the 8$^{th}$ object 632.

According to an embodiment of the present disclosure, a region where the 8$^{th}$ object 632 is displayed may show an animation effect which is expanded or reduced according to a change of the first range value of the displayed 7$^{th}$ object 630. For example, as an interval of the first range value is changed, the 8$^{th}$ object 632 may be changed according to form or numeral information or a rate change of the 7$^{th}$ object 630.

According to an embodiment of the present disclosure, a range of the 8$^{th}$ object 632 may be determined by combining standard deviation with an average value other than a maximum/minimum value. According to an embodiment of the present disclosure, colors and patterns of the $7^{th}$ object 630 and the $8^{th}$ object 632 may be changed to distinguish the $7^{th}$ object 630 (e.g., the progress bar) indicating the entire measurement range from the $8^{th}$ object 632 (e.g., a progress bar) indicating a value in which a user state is measured.

As described above, according to various embodiments of the present disclosure, the electronic device may include a memory configured to store at least one object and a processor configured to control a display to display a background screen object associated with measuring a heart rate among objects stored in the memory and to display a progress bar, corresponding to a predetermined first range value to display heart rate information, and a second object, corresponding to a second range value of heart rate information collected on the progress bar, on the first object. The processor may control the display to output the second object on a position of the first object, which is determined according to a ratio of the first range value to the second range value.

According to various embodiments of the present disclosure, the processor may control the display to display the second object in a form which is gradually expanded from a predetermined point of the second object, corresponding to a single value calculated from the collected heart rate information.

According to various embodiments of the present disclosure, the processor may control the display to display a third object, corresponding to the single value, on the second object.

According to various embodiments of the present disclosure, the processor may control the display to output numeral information corresponding to the first range value, numeral information corresponding to the second range value, and numeral information corresponding to the single value.

According to various embodiments of the present disclosure, the processor may control the display such that the numeral information is displayed as corresponding information by being changed every unit (e.g., 1) from a predetermined value (e.g., 0).

According to various embodiments of the present disclosure, the processor may adjust a change speed of the numeral information such that a time when the change is completed is identical to each other.

Figure 7:
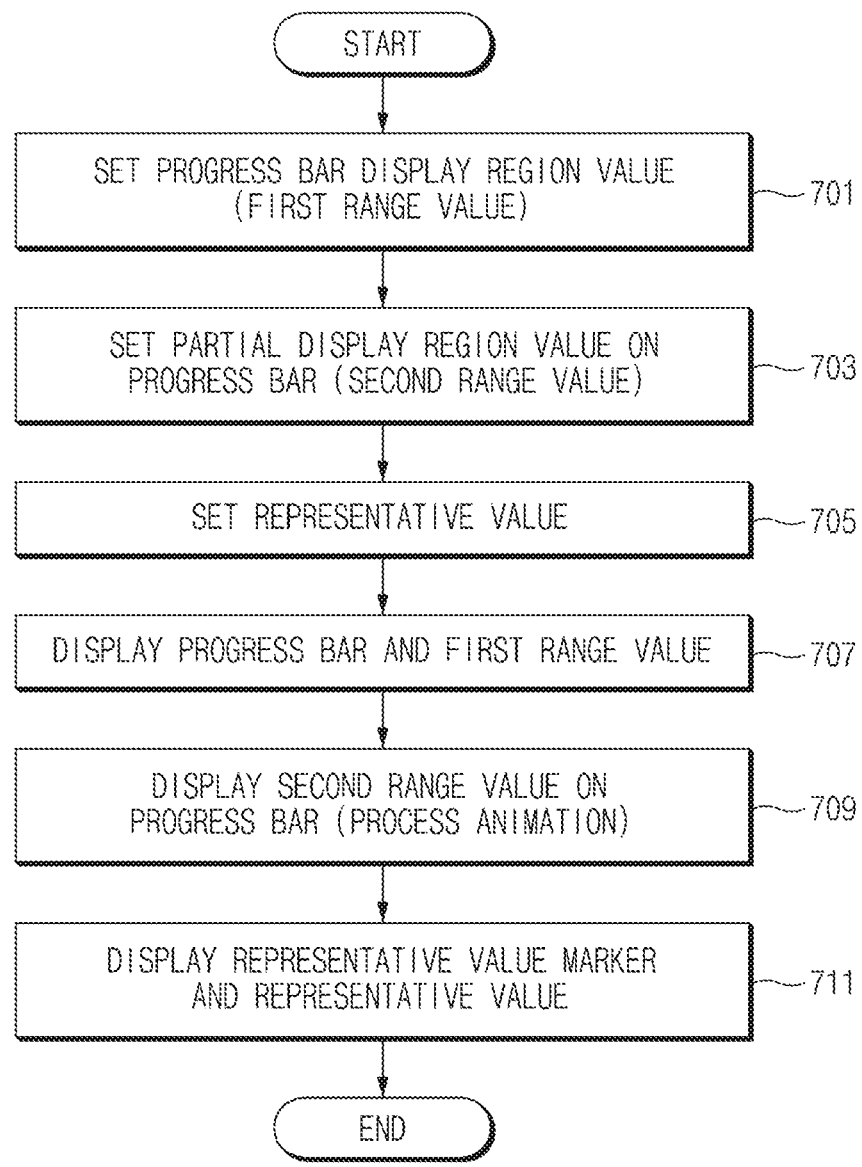
FIG. 7 is a flowchart illustrating an information display method using a progress bar according to various embodiments of the present disclosure.

FIG. 7 is a flowchart illustrating an information display method using a progress bar according to various embodiments of the present disclosure.

Referring to FIG. 7, in the information display method using the progress bar, an electronic device 100 of FIG. 1 may activate a predetermined function (e.g., a function of measuring biometric information, and the like). According to an embodiment of the present disclosure, the electronic device 100 may collect biometric information according to a function operation. If the collection of the biometric information is completed, or if biometric information of a predetermined degree is collected, in operation 701, the electronic device 100 may set a progress bar display region value. For example, the electronic device 100 may set the progress bar display region value according to the entire magnitude of the collected biometric information. According to an embodiment of the present disclosure, the electronic device 100 may set a region value of a certain size, including a maximum value and a minimum value of measured heartbeat, to a progress bar display region value.

In operation 703, the electronic device 100 may set a partial display region value on a progress bar. According to an embodiment of the present disclosure, the electronic device 100 may set a range (e.g., a range of a maximum value to a minimum value), which may include the entire collected biometric information, to the partial display region value. Alternatively, the electronic device 100 may set a range, which exclude a maximum value and a minimum value and includes the remaining values among the collected biometric information, to the partial display region value.

In operation 705, the electronic device 100 may set a representative value. For example, the electronic device 100 may set an average value or a median value of collected biometric information to the representative value.

In operation 707, the electronic device 100 may display a progress bar and a first range value. For example, the electronic device 100 may output a progress bar having a predetermined size and color on a predetermined position. The electronic device 100 may display the first range value on one side of the progress bar. In this operation, the electronic device 100 may output the first range value as an animation. According to an embodiment of the present disclosure, if the first range value is a range value of 40 to 120, the electronic device 100 may change and display the corresponding values from a predetermined numeral. For example, the electronic device 100 may first output 0 and may then output 1, 2, . . . 39, and 40 on a position where 40 of the first range value will be output. Also, the electronic device 100 may first output 0 and may then output 1, 2, . . . 119, and 120 on a position where 120 of the first range value will be output. The electronic device 100 may process a speed at which a numeral is changed in a different way such that a time when the outputting of 40 is completed is identical to a time when the outputting of 120 is completed. For example, the electronic device 100 may process a numeral change speed for outputting 120 to be three times faster than a numeral change speed for outputting 40. Therefore, the electronic device 100 may process a start value and an end value of a range such that a change completion time of the start value of the range is identical to a change completion time of the end value of the range and may display the start value and the end value of the range at a time when the change completion time of the start value is identical to the change completion time of the end value.

According to various embodiments of the present disclosure, the progress bar may be output as in a form in which a size or length is gradually changed from a constant position. For example, after an object of a constant size, corresponding to the progress bar, is output on a constant point of a display 160 of FIG. 1, it is displayed such that a size or length of the object is gradually increased to become a predetermined size.

In operation 709, the electronic device 100 may display a second range value on the progress bar. In this operation, the electronic device 100 may process an animation. For example, the electronic device 100 may calculate a size of an object corresponding to the second range value in proportion to a size of the progress bar. Also, the electronic device 100 may calculate a position of the second range value relative to the first range value of the progress bar. The electronic device 100 may output the object corresponding to the second range value on a position corresponding to the second range value of the progress bar. In this operation, the electronic device 100 may process the object to be gradually changed from one point of the progress bar to become a predetermined size. A numeric value corresponding to the second range value may be written on a region adjacent to the object. As a size of the object is changed, positions of a start value and an end value of the second range value may be changed. For example, a start value and an end value may be simultaneously displayed on a start point where the object is displayed. Therefore, the start value and the end value of the second range value may be overlapped and displayed on the start point. While a size or length of the object is gradually changed, the start value and the end value of the second range value may be moved and displayed according to a form in which the object is changed. As the change of the object is completed, if the object has the predetermined size, the start value and the end value of the second range value may be fixed and displayed. Herein, while numeric values of the start value and the end value are changed, the start value and the end value of the second range value may be displayed. According to various embodiments of the present disclosure, the start value and the end value of the second range value may have the same value as each other on a start point where the object is displayed. As the size of the object is changed, the start value and the end value of the second range value may be changed. For example, if the start value of the second range value is 60, if the end value is 70, and if an object is displayed on a 65 point, the start value and the end value of the second range value may be first output as 65 to be identical to each other. Thereafter, the start value of the second range value may be changed to 65, 64, 63, . . . 60. The end value of the second range value may be changed to 65, 66, 67, . . . 70. According to various embodiments of the present disclosure, the start value and the end value of the second range value may overlapped and displayed as 60 and 70 on the 65 point, respectively. While display positions of the start value 60 and the end value 70 of the second range value are changed as a size of the object is changed, the start value and the end value of the second range value may be displayed on positions adjacent to edge regions of the object. A start point where the object is displayed may be, for example, a position corresponding to a representative value on a progress bar.

In operation 711, the electronic device 100 may display a representative value marker and a representative value. For example, the electronic device 100 may output the representative value marker on the object corresponding to the second range value. The electronic device 100 may output the representative value on a region adjacent to the representative value marker.

According to various embodiments of the present disclosure, the electronic device 100 may output the first range value at the same time as a time when the second range value is displayed. Also, the electronic device 100 may perform an operation such that a time when a change of the first range value is completed is identical to a time when displaying of the second range value is completed. In this regard, the electronic device 100 may adjust a change speed of a start value and an end value of the first range value and a change speed of the start value and the end value of the second range value in a different way and may display the representative value marker and the representative value at a time when a change of an object, corresponding to the first range value and the second range value, is completed. According to an embodiment of the present disclosure, the electronic device 100 may process a time when the representative value marker and the representative value are displayed such that displaying of the first range value and a change of the object, corresponding to the second range value, and the second range value are completed.

Figure 8:
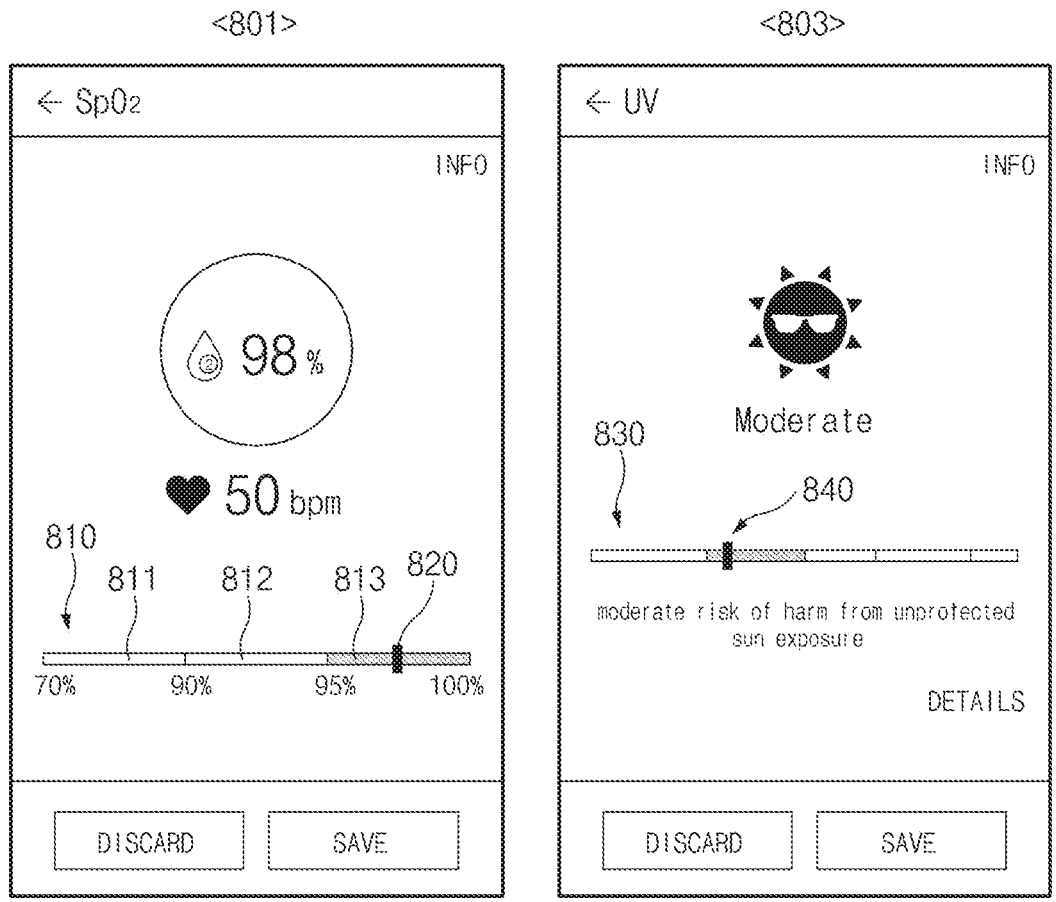
FIG. 8 is a drawing illustrating an information display method in a plurality of regions according to various embodiments of the present disclosure.

FIG. 8 is a drawing illustrating an information display method in a plurality of regions according to various embodiments of the present disclosure.

Referring to FIG. 8, an electronic device 100 of FIG. 1 may output a first progress bar 810, including a plurality of sub-objects 811 to 813, on a screen 801. The screen 801 may display, for example, a result of measuring $SpO_2$ using the first progress bar 810 according to an embodiment of the present disclosure. A first range corresponding to the first progress bar 810 may be a range of 70% to 100% and may include the three sub-objects 811 to 813. The first sub-object 811 of the sub-objects 811 to 813 may mean that $SpO_2$ is low. The second sub-object 812 of the sub-objects 811 to 813 may mean that $SpO_2$ is normal, and the third sub-object 813 of the sub-objects 811 to 813 may mean that $SpO_2$ is good. Also, a $SpO_2$ representative value of a measured result may be 98% and may be displayed on the third sub-object 813. As described above, the first progress bar 810 may be drawn with a thick line segment or figure having round opposite ends. The sub-objects 811 to 813 may correspond to divided regions of the first progress bar 810. A representative value marker 820 may be displayed in response to a corresponding sub-object (e.g., the third sub-object 813). According to an embodiment of the present disclosure, attributes of the third sub-object 813 on which the representative value marker 820 is displayed may be changed on a representative value. For example, a way of displaying the third sub-object 813 may be a way of being gradually changed relative to the representative value marker 820. Alternatively, the way of displaying the third sub-object 813 may be a way of filling a constant region of the first progress bar 810 with a predetermined color relative to a point where the representative value marker 820 is displayed. Alternatively, the way of displaying the third sub-object 813 may be a way of gradually filling the third sub-object 813 with a predetermined color from an edge of the third sub-object 813 to a point where the representative value marker 820 is displayed.

According to an embodiment of the present disclosure, the electronic device 100 may display a result of measuring UV on a screen 803. Herein, a first range of a second progress bar 830 may be a range of a low level to a high level and may be configured with five sub-objects. Herein, a representative value object 840 may be disposed on a moderate region in response to the measured result. According to an embodiment of the present disclosure, before the representative value object 840 is displayed, the moderate region to display the representative value object 840 may have a form which is gradually changed through an animation effect from the representative value object 840 which is a start point.

According to various embodiments of the present disclosure, the electronic device 100 may display a pie graph, a bar graph, and the like as objects, which are replaced with a progress bar, or as added objects. In case of the pie graph, a filled range may be changed relative to a start point. According to an embodiment of the present disclosure, the start point may be simultaneously or successively provided to a user using a different color or a different pattern.

Figure 9:
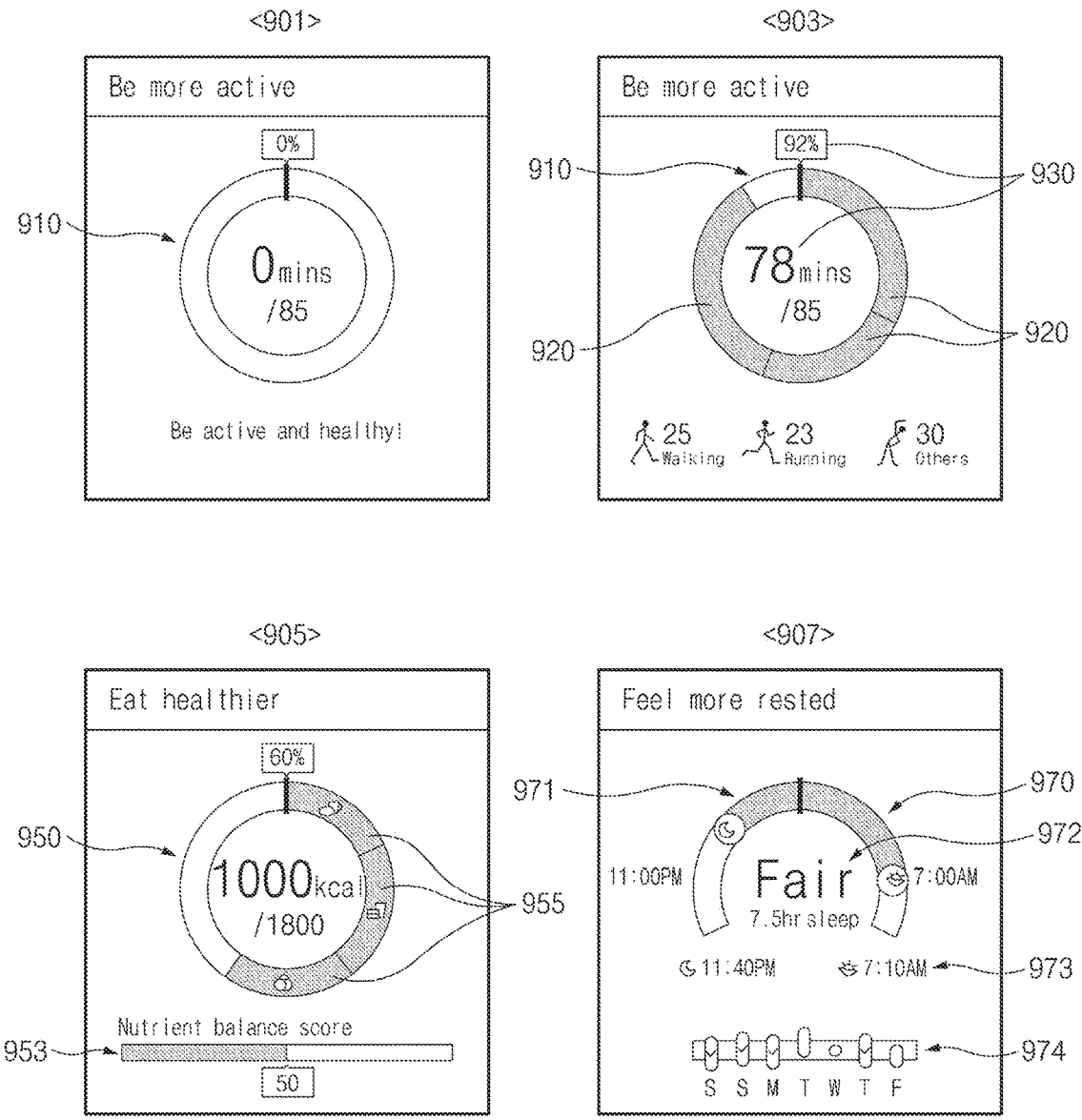
FIG. 9 is a drawing illustrating an information display method in a plurality of regions according to various embodiments of the present disclosure.

FIG. 9 is a drawing illustrating an information display method in a plurality of regions according to various embodiments of the present disclosure.

Referring to FIG. 9, an electronic device 100 of FIG. 1 may output a circular progress bar, a pie chart having an empty middle, or various arc-shaped objects. According to an embodiment of the present disclosure, the electronic device 100 may output a circular progress bar 910, which displays an exercise level (or an exercise execution time) and an exercise type, on a screen 901. The exercise level or the exercise type may be input or sensed through a user input or a motion sensor and a biometric sensor. For example, a goal exercise level, which is set by a user or is automatically set according to biometric information of him or her, may be 85 minutes per day. In this case, a first range may be set (e.g., a range of 0 minute to 85 minutes) in response to the goal exercise level. Also, if there no exercise level, a representative value may be 0.

The electronic device 100 may display an exercise type and an exercise time, which are input by the user or are recognized through sensing information, on a screen 903. For example, the electronic device 100 may display a state where the total exercise time of 78 minutes (e.g., walking of 25 minutes, running of 23 minutes, other exercises of 30 minutes) is achieved and 92% is achieved to a goal exercise level. In this case, the electronic device 100 may output a second object 920. The second object 920 may include 3 sub-regions (e.g., a walking sub-region, a running sub-region, and the other sub-region). The second object 920 may be configured according to a rate such that a rate of the walking sub-region is 29.4%, a rate of the running sub-region is 27.1%, and a rate of the other sub-region is 35.3%. The sub-regions of the second object 920 may be successively disposed according each rate on the circular progress bar 910.

A representative value may be 92%, and a representative value marker 930 may be disposed on a start point or an end point of a region, where the second object 920 is displayed, using attributes (e.g., a gray tone) which are distinguished from the circular progress bar 910 and the second object 920. Numeral information corresponding to the representative value may be displayed on a region adjacent to a position where the representative value marker 930 is displayed.

According to an embodiment of the present disclosure, the electronic device 100 may visually display biometric information through an animation effect. If a result of measuring an exercise level through a motion sensor is calculated, the electronic device 100 may calculate rates of the second object 920 and may display an end region of the second object using predetermined animation attributes. For example, the electronic device 100 may display the second object 920 to increase a region of the second object 920 through an animation effect from the representative value marker 930 displayed on the circular progress bar 910 to a previously calculated display region of the second object 920 and to fill the inside of the second object 920 with a predetermined color or effect. Alternatively, the electronic device 100 may successively display the second object 920 per sub-region. According to various embodiments of the present disclosure, the animation effect may be applied to only a corresponding sub-region according to an updated exercise type among the sub-regions of the second object 920.

According to an embodiment of the present disclosure, a measured exercise level may exceed a goal exercise level. In this case, the electronic device 100 may change the first range corresponding to the circular progress bar 910 to the measured exercise level. For example, if the sum of a second range exceeds the first range, the first range may be changed to one or more of the second range or the sum of the second range.

According to various embodiments of the present disclosure, the electronic device 100 may display three second objects 955 (e.g., breakfast, lunch, and refreshments) on a circular progress bar 950 on a screen 905. Images, such as a size or a form, of the second objects 955 may be changed according to input information. Also, the electronic device 100 may output a separate linear progress bar 953. The linear progress bar 953 may indicate predetermined balance (e.g., balance between vegetable intake and meat intake or balance among carbohydrate intake, protein intake, and fat intake) according to kinds of intake foods According to various embodiments of the present disclosure, the electronic device 100 may output an arc progress bar 970 corresponding to time on a screen 907. The arc progress bar 970 may be generated in response to a sleeping hour range 971 accommodated to a user. The electronic device 100 may display a second object corresponding to a real sleeping start hour and a real sleeping end hour. The electronic device 100 may output a representative value object 972 corresponding to a qualitative evaluation (e.g., fair) according to the total sleeping hour (e.g., 7.5 hours) or a goal sleeping hour to an amount of achievement. The electronic device 100 may output a numeral information object 973 corresponding to a sleeping start and a sleeping end. The electronic device 100 may output a sleeping quality object 974 corresponding to a sleeping pattern or a sleeping depth for one week.

According to various embodiments of the present disclosure, in connection with outputting the above-mentioned progress bar and dynamically displaying the second object on the progress bar, the electronic device 100 may display the second object in real time using previously measured accumulation results while biometric information is measured. Alternatively, the electronic device 100 may display the second object according to an accumulated result measured after the measurement of biometric information is completed.

Figure 10:
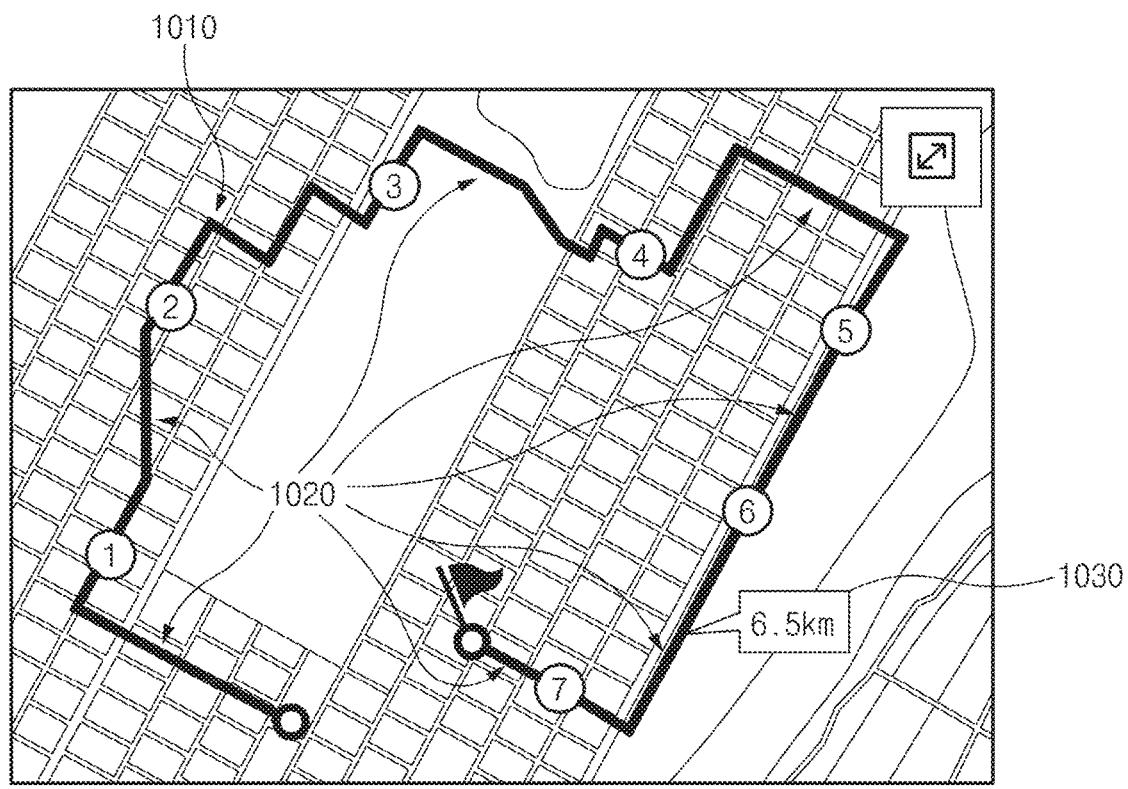
FIG. 10 is a drawing illustrating a map-based information display method according to various embodiments of the present disclosure.

FIG. 10 is a drawing illustrating a map-based information display method according to various embodiments of the present disclosure.

Referring to FIG. 10, an electronic device 100 of FIG. 1 may output a route object 1010 on a map. The route object 1010 may be generated according to location information collected according to a movement of a user or information set to move by him or her. The route object 1010 may include second objects 1020 (e.g., a 1 km unit). In this case, the electronic device 100 may determine its position using a position sensor and may display a representative value marker 1030, which uses current position information as a representative value, for an accumulated movement distance on a route or a current position.

The representative value marker 1030 may be displayed in response to the occurrence of a predetermined event. At a time when the representative value marker 1030 is displayed, the second object 1020 where the representative value marker 1030 is located may be displayed as an animation. For example, the second object 1020 (e.g., between No. 6 and No. 7) where the representative value marker 1030 is located may be displayed in a form which is gradually increased relative to the representative value marker 1030. Also, a color of the second object 1020 where the representative value marker 1030 is located may differ from those of other objects. Alternatively, the second object 1020 where the representative value marker 1030 is located may be changed according to a movement speed of the electronic device 100. Additionally or alternatively, each of the second objects 1020 may have a predetermined color according to a movement speed of the electronic device 100.

According to various embodiments of the present disclosure, to display a progress bar or a second object as an animation on a display 160 of FIG. 1, the electronic device 100 may perform physical calculation using a physics engine module 180 of FIG. 1. For example, to display an animation clockwise in a position where a representative value marker is displayed, the electronic device 100 may set a fluid pressure in the representative value marker and may set a low end of the display 160 in a gravity direction. Therefore, the animation may express an effect in which it is increased in speed from a start point to a progress bar point corresponding to a low end of a screen and is gradually decreased in speed if the bottom is passed.

According to various embodiments of the present disclosure, information provided through an object may include information measured through a sensor of the electronic device 100 or temperature, humidity, insolation, rainfall, a UV index, and the like which are transmitted through a network, other than state information of the user.

Figure 11:
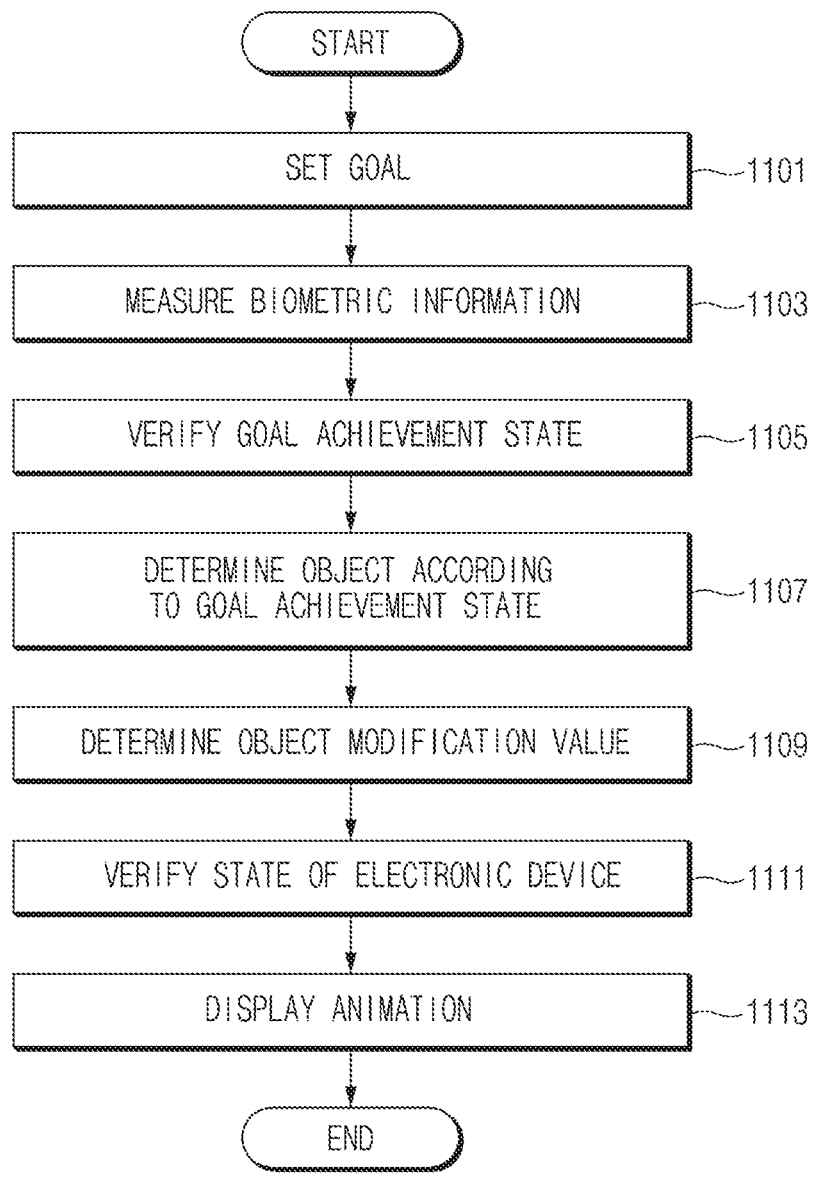
FIG. 11 is a flowchart illustrating an animation processing method using physical attributes according to various embodiments of the present disclosure.

FIG. 11 is a flowchart illustrating an animation processing method using physical attributes according to various embodiments of the present disclosure.

Referring to FIG. 11, in connection with the animation processing method, in operation 1101, an electronic device 100 of FIG. 1 may set a goal in response to a user input or scheduled information. In operation 1103, the electronic device 100 may activate a predetermined sensor and may measure biometric information according to the predetermined sensor. In operation 1105, the electronic device 100 may verify a goal achievement state.

In operation 1107, the electronic device 100 may determine an object according to the goal achievement state. For example, the electronic device 100 may determine an object to be output in a different way according to whether a user achieves the goal or does not achieve the goal.

In operation 1109, the electronic device 100 may calculate an object modification value according to characteristics of the measured biometric information. For example, the electronic device 100 may determine physical characteristics (e.g., gravity, fluid pressure, and the like) to be applied in response to a type of the biometric information. Also, the electronic device 100 may determine that any animation effect is applied in response to a type of biometric information.

In operation 1111, the electronic device 100 may verify its state. For example, the electronic device 100 may verify whether it currently takes any pose. In operation 1113, the electronic device 100 may display a predetermined animation by applying physical characteristics determined according to its current state to an object to be output.

Figure 12:
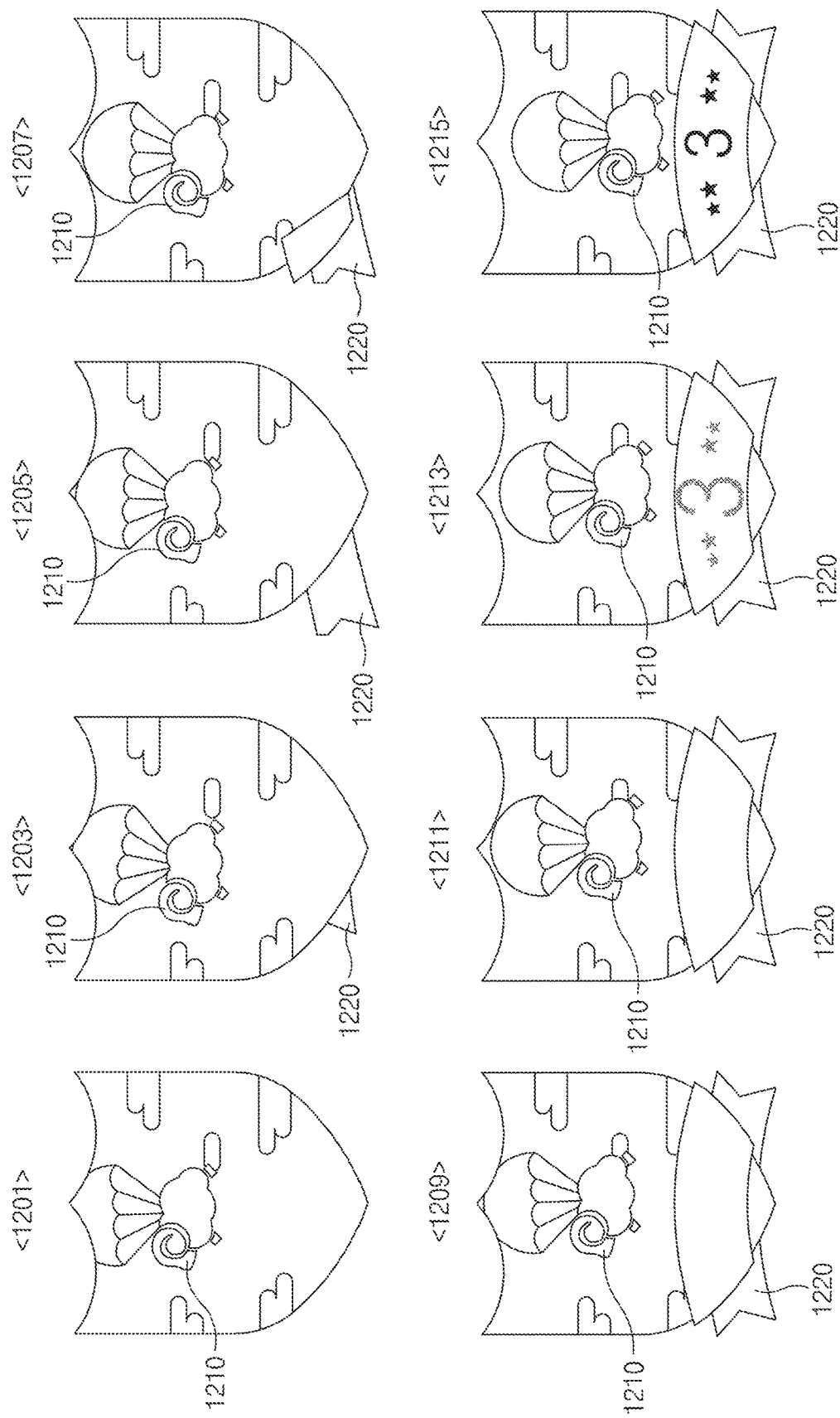
FIG. 12 is a drawing illustrating the displaying of deep sleeping degree related information according to various embodiments of the present disclosure.

FIG. 12 is a drawing illustrating the displaying of deep sleeping degree related information according to various embodiments of the present disclosure.

Referring to FIG. 12, an electronic device 100 of FIG. 1 may display a movement form of a first object 1210 through states 1201 to 1215. In this case, the electronic device 100 may output a movement of the first object 1210 according to a physical characteristic. In this regard, the electronic device 100 may collect sensing information associated with the physical characteristic, for example, a gravity characteristic. As shown in FIG. 12, the electronic device 100 may display a movement of the first object 1210 according to the collected sensing information. In connection with FIG. 12, for example, the first object 1210 may have a form which is actually or approximately vertically disposed. The electronic device 100 may display a movement of the first object 1210 to which a gravity characteristic according to the vertical disposal is applied. Alternatively, the electronic device 100 may collect biometric information about a pose state (e.g., a standing state) of a user and may display a movement of the first object 1210 to which a gravity characteristic according to the collected biometric information is applied.

In addition, in state 1203, if the first object 1210 is moved to a constant size or more, the electronic device 100 may display a second object 1220. The second object 1220 may modified and displayed in response to a movement distance of the first object 1210. Alternatively, if the second object 1220 is moved to a constant distance or more, it may be displayed once. The second object 1220 may output, for example, achieved goal level information (e.g., information indicating that a sleeping degree of three successive days is achieved as a good state).

In connection with the above-mentioned display and control, the electronic device 100 may calculate a trajectory and a speed of a parachute according to exercise strength or an air volume and may control motion of an object (e.g., a sheep which uses a parachute) according to the calculated trajectory and speed, using a physics engine. In this case, the electronic device 100 may provide various types of animation effects according to a state of the electronic device 100 or a physiological state of a user by setting physical attributes according to the physiological state of him or her through measurement of biometric information.

In connection with FIG. 12, biometric information of the user measured by the electronic device 100 may be a sleeping hour or a deep sleeping degree. The electronic device 100 may determine a start and end of sleep through a user input or one or more of a motion sensor, a respiration sensor, an EEG sensor, and a breath sensor (or a microphone) and may measure an hour when the user sleeps. The electronic device 100 may determine quality (rapid eye movement (REM) sleep, light sleep, and the like) of sleep through the EEG sensor and the respiration sensor.

The user may set a goal of specific biometric information. For example, the user may enter a sleeping start hour and a sleeping end hour through a user interface of the electronic device 100 and may store the sleeping start hour and the sleeping end hour in a memory 130 of FIG. 1. If biometric information (e.g., an amount of sleep) is measured through the electronic device 100 or another sensor or a remote electronic device functionally connected with the electronic device 100, the electronic device 100 may collect the measured biometric information.

A processor 120 of the electronic device 100 may determine whether biometric information of the user meets a set goal according to the measured biometric information and may verify a goal achievement state. In this regard, the electronic device 100 may verify a plurality of conditions in connection with outputting the first object 1210. For example, in case of an amount of sleep, if all of a set sleeping hour and a set sleeping end hour are met (e.g., if a set event is performed within 15 minutes before and after a set time), the electronic device 100 may determine the target achievement state as a good state. Alternatively, if only one of the sleeping start hour or the sleeping end time is met and if a certain sleeping hour (e.g., six hours) is met, the electronic device 100 may determine the goal achievement state as a normal state (or a fair state). Alternatively, if a predetermined sleeping hour is not met or all of the sleeping start time and the sleeping end time are not met, the electronic device 100 may determine the goal achievement state as a bad state. The goal achievement state may include sleep related information (e.g., a sleeping star hour, a sleeping end hour, and the total sleeping hour).

The electronic device 100 may determine an object to be displayed on a display 160 of FIG. 1 and may determine an object display form according to the goal achievement state. For example, if it is determined that achieved goal attributes are associated with sleep, an object associated with sleep may be selected. For example, the object may include graphic elements corresponding to information such as sleep, an exercise time, an exercise level, nutrition, an exercise speed, and an exercise route. An object which has a predetermined correlation among a plurality of objects may be selected in connection with the goal achievement state. For example, as shown in FIG. 12, the first object 1210 may be selected.

If the object is determined, a display form of the corresponding object may be determined. For example, the electronic device 100 may display a sheep such that the sheep which uses a parachute is swung and falls to the ground on a sleeping degree related animation of FIG. 12. To display this, the electronic device 100 may set a gravity direction to a low end of a shield icon and may calculate a falling speed of the first object 1210. For example, the electronic device 100 may collect settings such as acceleration of gravity associated with the first object 1210, an air resistance coefficient of a virtual parachute, a weight of a virtual sheep, a weight of a virtual parachute, a width and period of a virtual pendulum movement (e.g., a cord length and a swing angle of a parachute, a foot length and a swing angle for calculating swing of a sheep, and the like). According to an embodiment of the present disclosure, this setting of the object may be preset. Alternatively, the settings of the object may be measured or may be set using one or more of biometric information entered by the user.

According to an embodiment of the present disclosure, the electronic device 100 may set the object in connection with a sleeping hour of the user and a falling hour. For example, when a sleeping hour is longer or quality of sleep is better (e.g., determination through a motion degree during a sleeping period or depth of sleep, and the like), the electronic device 100 may change air resistance, weight of an object, and a value of acceleration of gravity to reduce a falling speed. Alternatively, when a sleeping hour is shorter, the electronic device 100 may broaden a swing angle to emphasize a speed and form at which a sheep is swung to be shown faster and better and may display a cord length of a parachute to be shortened. Alternatively, if a sleeping hour is short, the electronic device 100 may set a level of an air volume to be high in inverse proportion to the sleeping hour or may automatically change a swing angle or a cord length of a parachute which has correlation with the sleeping time.

For example, swing of a sheep which uses a parachute may be obtained through Equation 1 below.

$$T = 2\pi \sqrt{\frac{l}{g}} \quad \text{Equation 1}$$

Herein, g may be set acceleration of gravity, l may be a length of a parachute, and T may be a period of a pendulum movement.

The displaying and setting of the object may be applied to the second object (e.g., a ribbon). For example, a numeral displayed on the ribbon may display that a goal is achieved for three successive days. A speed at which the ribbon is drawn, elasticity (e.g., a modification speed) of the ribbon, and the like may be changed according to the number of successive goal achievement days.

If an object and the displaying and setting of the object are determined, a state of the electronic device 100 may be verified and a direction to which physical attributes are applied may be determined. A display setting direction of the object may be changed according to a pose or orientation of the electronic device 100, attributes (e.g., the number of horizontal pixels and the number of vertical pixels) of the display 160, and the like. For example, the electronic device 100 may change a region and a size to be displayed on an animation according to setting of a horizontal mode and a vertical mode.

According to various embodiments of the present disclosure, if biometric information is quality of sleep, as shown in FIG. 12, a shield, a sheep which uses a parachute, or a ribbon as an object associated with sleep may be selected as an object indicating sleep of the user. As a result of the quality of sleep of the user, the electronic device 100 may output various types of shield images, various types of sheep using parachutes, and various types of ribbons. Level information corresponding to the quality of sleep of the user may be displayed on the ribbon. In a process of displaying the ribbon to cover a shield image, an effect that a force for tying the ribbon is applied may be provided. According to an embodiment of the present disclosure, a direction in which a sheep which uses a parachute is moved may be changed in response to result values of sensors, mounted in the electronic device 100, which may measure gravity, a frictional force, speed, acceleration, and the like.

According to various embodiments of the present disclosure, the electronic device 100 may change a visual effect provided to the user by reflecting a deep sleeping degree to a shape and motion of a sheep.

According to various embodiments of the present disclosure, if a deep sleeping degree is high, the electronic device 100 may display a numeral of a deep sleeping level indicating a ribbon in a different way. Also, the electronic device 100 may provide an effect of recognizing a deep sleeping degree as a changed amount of a moved object by changing strength of tying a ribbon.

According to various embodiments of the present disclosure, the electronic device 100 may change a motion degree and direction of a sheep which uses a moved parachute by reflecting environment information around the user. If an air volume is strong, the electronic device 100 may strengthen a swing degree of a sheep which uses a parachute.

As described above, according to various embodiments of the present disclosure, the electronic device may include a memory configured to store at least one object to be output in connection with a sleeping state and a processor configured to control a display to display a background screen object associated with the sleeping state among objects stored in the memory and to display a second object associated with an amount of sleep. The processor may control the display to output at least one of a position, a size, a motion form, or a speed of the second object in a different way according to relation between a set goal value and an amount of sleep in connection with the sleeping state.

The processor may determine at least one physical characteristic in connection with a state of a human body associated with a state of the electronic device or the sleeping state and may control the display to change a display effect of the second object according to the physical characteristic.

Figure 13:
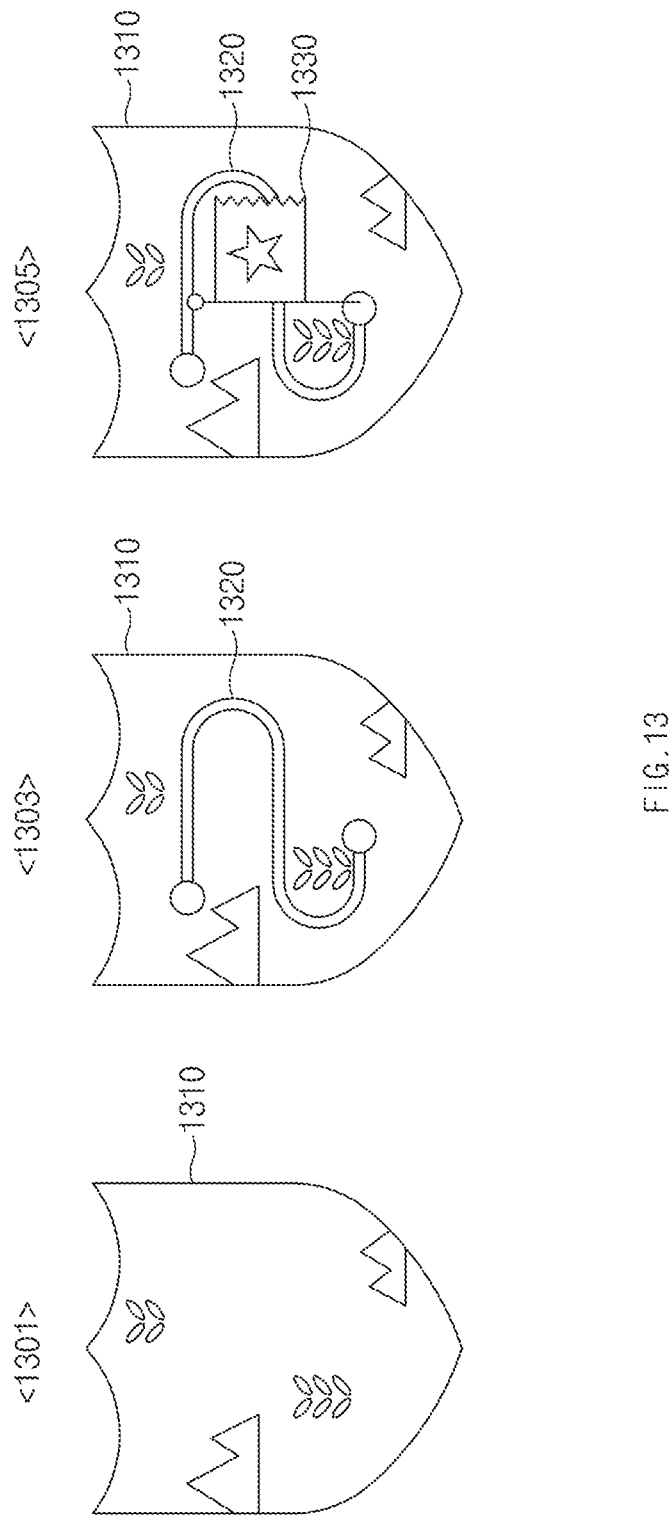
FIG. 13 is a drawing illustrating the displaying of animation information according to biometric information according to various embodiments of the present disclosure.

FIG. 13 is a drawing illustrating the displaying of animation information according to biometric information according to various embodiments of the present disclosure.

Referring to FIG. 13, according to an embodiment of the present disclosure, a certain heart rate and certain duration may be set as a goal. If the heart rate or more is maintained during the certain duration or more by a heart rate sensor and a timer, an electronic device 100 of FIG. 1 may determine that the goal is achieved. If a goal heart rate is maintained during a certain time, the electronic device 100 may determine that the goal is achieved and may select a certain object (e.g., an animation element of FIG. 13) in connection with a heart rate in which the goal is achieved.

According to an embodiment of the present disclosure, the electronic device 100 may select a first object 1310 (e.g., a shield) as shown in state 1301, a second object 1320 (e.g., a road) as shown in state 1303, and a third object 1330 (e.g., a flag) as shown in state 1305, to start a measured heart rate of a user. To indicate the measured heart rate of the user, the electronic device 100 may display the second object 1320 from a specific point on the first object 1310. If the displaying of the second object 1320 is completed, the electronic device 100 may display the third object 1330 on a specific point on the second object 1320. In this case, the electronic device 100 may provide an effect of swinging a flagpole left and right in connection with displaying the third object 1330 and may display the flagpole to stop the swinging after a constant time elapses.

According to various embodiments of the present disclosure, if a measured heart rate is a constant level or more, the electronic device 100 may strengthen a degree in which a flag is swung left and right to indicate that heartbeat of the user is fast.

According to various embodiments of the present disclosure, if stress, hastiness, and the like of the user are extracted from a measured heart rate, the electronic device 100 may change the swing of the third object 1330 and a speed at which the second object 1320 is drawn according to an emotional state of the user.

As described above, according to various embodiments of the present disclosure, the electronic device 100 may provide a UI, which interacts with the user, to the user in real time using a sensor mounted on the electronic device 100 and surrounding information of the user and state information of the user such as a setting and input method of the user and may provide various effects. The electronic device 100 may improve visibility and readability to the user and may provide a more engaging user experience.

Figure 14:
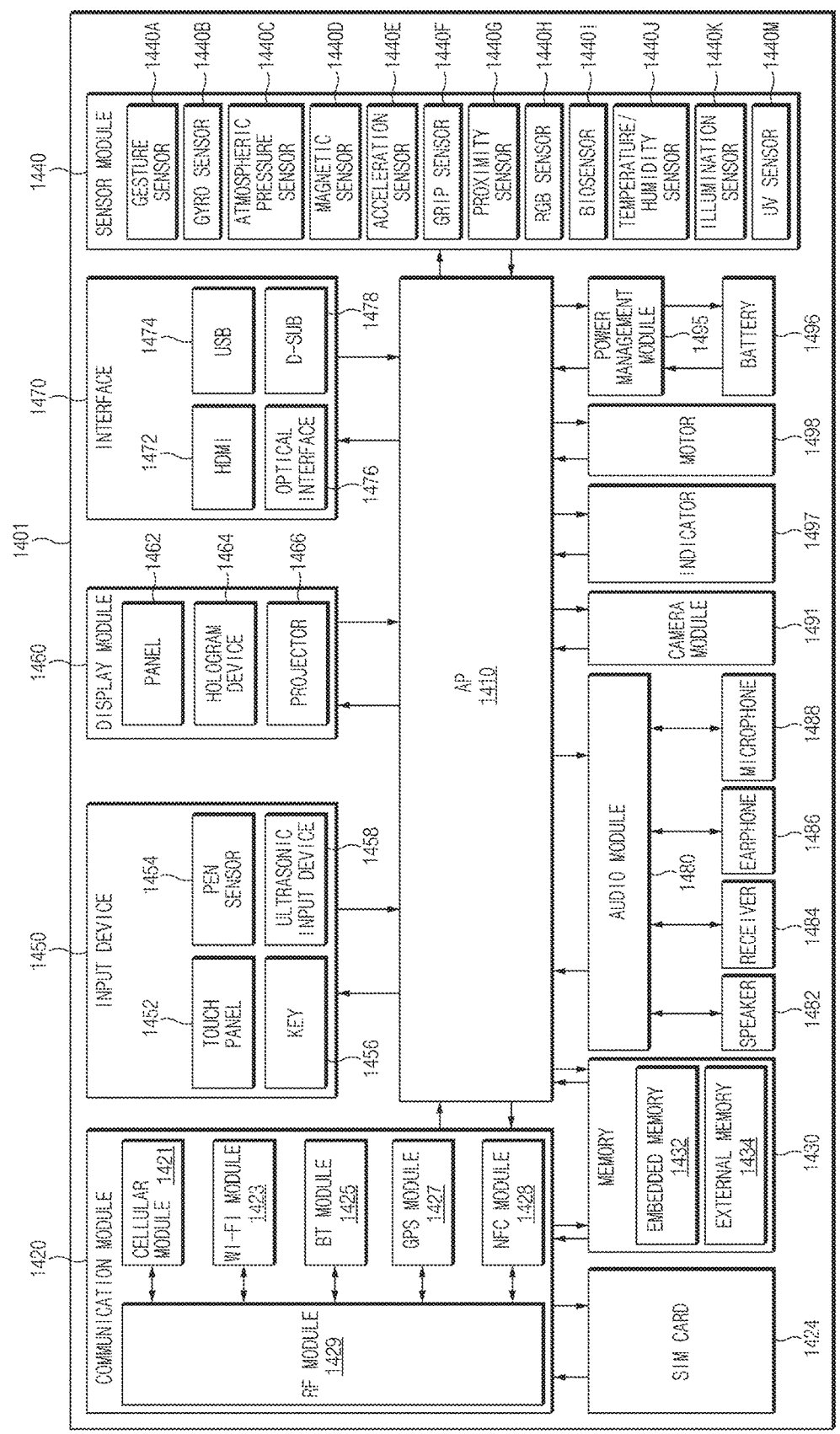
FIG. 14 is a block diagram illustrating a configuration of an electronic device according to various embodiments of the present disclosure.

FIG. 14 is a block diagram illustrating a configuration of an electronic device according to various embodiments of the present disclosure.

Referring to FIG. 14, an electronic device 1401 may include, for example, all or a part of an electronic device 101 shown in FIG. 1. The electronic device 1401 may include one or more APs 1410, a communication module 1420, a subscriber identification module (SIM) card 1424, a memory 1430, a sensor module 1440, an input device 1450, a display 1460, an interface 1470, an audio module 1480, a camera module 1491, a power management module 1495, a battery 1496, an indicator 1497, and a motor 1498.

The AP 1410 may drive, for example, an OS or an application program to control a plurality of hardware or software components connected thereto and may process and compute a variety of data. The AP 1410 may be implemented with, for example, a system on chip (SoC). According to an embodiment of the present disclosure, the AP 1410 may further include a graphics processing unit (GPU) (not shown) and/or an image signal processor. The AP 1410 may include at least some (e.g., a cellular module 1421) of the components shown in FIG. 14. The AP 1410 may load instructions or data received from at least one of other components (e.g., a non-volatile memory) to a volatile memory to process the data and may store various data in a non-volatile memory.

The communication module 1420 may have the same or similar configuration as or to that of a communication interface 170 of FIG. 1. The communication module 1420 may include, for example, the cellular module 1421, a Wi-Fi module 1423, a Bluetooth (BT) module 1425, a GPS module 1427, an NFC module 1428, and an RF module 1429.

The cellular module 1421 may provide, for example, a voice call service, a video call service, a text message service, or an Internet service, and the like through a communication network. According to an embodiment of the present disclosure, the cellular module 1421 may identify and authenticate the electronic device 1401 in a communication network using a SIM (e.g., the SIM card 1424). According to an embodiment of the present disclosure, the cellular module 1421 may perform at least a part of functions which may be provided by the AP 1410. According to an embodiment of the present disclosure, the cellular module 1421 may include a CP.

The Wi-Fi module 1423, the BT module 1425, the GPS module 1427, or the NFC module 1428 may include, for example, a processor for processing data transmitted and received through the corresponding module. According to various embodiments of the present disclosure, at least a part (e.g., two or more) of the cellular module 1421, the Wi-Fi module 1423, the BT module 1425, the GPS module 1427, or the NFC module 1428 may be included in one integrated chip (IC) or one IC package.

The RF module 1429 may transmit and receive, for example, a communication signal (e.g., an RF signal). Though not shown, the RF module 1429 may include, for example, a transceiver, a power amplifier module (PAM), a frequency filter, or a low noise amplifier (LNA), or an antenna, and the like. According to an embodiment of the present disclosure, at least one of the cellular module 1421, the Wi-Fi module 1423, the BT module 1425, the GPS module 1427, or the NFC module 1428 may transmit and receive an RF signal through a separate RF module.

The SIM card 1424 may include, for example, a card which includes a SIM and/or an embedded SIM. The SIM card 1424 may include unique identification information (e.g., an integrated circuit card identifier (ICCID)) or subscriber information (e.g., an international mobile subscriber identity (IMSI)).

The memory 1430 (e.g., a memory 130 of FIG. 1) may include, for example, an embedded memory 1432 or an external memory 1434. The embedded memory 1432 may include at least one of, for example, a volatile memory (e.g., a dynamic random access memory (DRAM), a static RAM (SRAM), a synchronous DRAM (SDRAM), and the like), or a non-volatile memory (e.g., a one-time programmable read only memory (OTPROM), a PROM, an erasable and programmable ROM (EPROM), an electrically erasable and programmable ROM (EEPROM), a mask ROM, a flash ROM, a flash memory (e.g., a NAND flash memory or a NOR flash memory, and the like), a hard drive, or a solid state drive (SSD)).

The external memory 1434 may further include a flash drive, for example, a compact flash (CF), a secure digital (SD), a micro-SD, a mini-SD, an extreme digital (xD), or a memory stick, and the like. The external memory 1434 may functionally and/or physically connect with the electronic device 1401 through various interfaces.

The sensor module 1440 may measure, for example, a physical quantity or may detect an operation state of the electronic device 1401, and may convert the measured or detected information to an electric signal. The sensor module 1440 may include at least one of, for example, a gesture sensor 1440A, a gyro sensor 1440B, an atmospheric pressure sensor 1440C, a magnetic sensor 1440D, an acceleration sensor 1440E, a grip sensor 1440F, a proximity sensor 1440G, a color sensor 1440H (e.g., RGB sensor), a biosensor 1440I, a temperature/humidity sensor 1440J, an illumination sensor 1440K, or a UV sensor 1440M. Additionally or alternatively, the sensor module 1440 may further include, for example, an e-nose sensor (not shown), an EMG sensor (not shown), an EEG sensor (not shown), an ECG sensor (not shown), an IR sensor (not shown), an iris sensor (not shown), and/or a fingerprint sensor (not shown), and the like. The sensor module 1440 may further include a control circuit for controlling at least one or more sensors included therein. According to various embodiments of the present disclosure, the electronic device 1401 may further include a processor configured to control the sensor module 1440, as a part of the AP 1410 or to be independent of the AP 1410. While the AP 1410 is in a sleep state, the electronic device 1410 may control the sensor module 1440.

The input device 1450 may include, for example, a touch panel 1452, a (digital) pen sensor 1454, a key 1456, or an ultrasonic input device 1458. The touch panel 1452 may recognize a touch input using at least one of, for example, a capacitive detecting method, a resistive detecting method, an IR detecting method, or an ultrasonic detecting method. Also, the touch panel 1452 may further include a control circuit. The touch panel 1452 may further include a tactile layer and may provide a tactile reaction to a user.

The (digital) pen sensor 1454 may be, for example a part of a touch panel or may include a separate sheet for recognition. The key 1456 may include, for example, a physical button, an optical key, or a keypad. The ultrasonic input device 1458 may allow the electronic device 1401 to detect a sound wave using a microphone (e.g., a microphone 1488) and to verify data through an input tool generating an ultrasonic signal.

The display module 1460 (e.g., a display 160 of FIG. 1) may include a panel 1462, a hologram device 1464, or a projector 1466. The panel 1462 may include the same or similar configuration as or to that of the display 160. The panel 1462 may be implemented to be, for example, flexible, transparent, or wearable. The panel 1462 and the touch panel 1452 may be integrated into one module. The hologram device 1464 may show a stereoscopic image in a space using interference of light. The projector 1466 may project light onto a screen to display an image. The screen may be positioned, for example, inside or outside the electronic device 1401. According to an embodiment of the present disclosure, the display 1460 may further include a control circuit for controlling the panel 1462, the hologram device 1464, or the projector 1466.

The interface 1470 may include, for example, an HDMI 1472, a USB 1474, an optical interface 1476, or a D-subminiature 1478. The interface 1470 may be included in, for example, a communication interface 170 shown in FIG. 1. Additionally or alternatively, the interface 1470 may include, for example, a mobile high definition link (MHL) interface, an SD card/multimedia card (MMC) interface, or an infrared data association (IrDA) standard interface.

The audio module 1480 may convert a sound and an electric signal in dual directions. At least a part of components of the audio module 1480 may be included in, for example, an input device 140 or an output device 150 shown in FIG. 1. The audio module 1480 may process sound information input or output through, for example, a speaker 1482, a receiver 1484, an earphone 1486, or the microphone 1488, and the like.

The camera module 1491 may be a device which captures a still picture and a moving picture. According to an embodiment of the present disclosure, the camera module 1491 may include one or more image sensors (not shown) (e.g., a front sensor or a rear sensor), a lens (not shown), an image signal processor (ISP) (not shown), or a flash (not shown) (e.g., an LED or a xenon lamp).

The power management module 1495 may manage, for example, power of the electronic device 1401. According to an embodiment of the present disclosure, though not shown, the power management module 1495 may include a power management integrated circuit (PMIC), a charger IC or a battery or fuel gauge. The PMIC may have a wired charging method and/or a wireless charging method. The wireless charging method may include, for example, a magnetic resonance method, a magnetic induction method, or an electromagnetic method, and the like. An additional circuit for wireless charging, for example, a coil loop, a resonance circuit, or a rectifier, and the like may be further provided. The battery gauge may measure, for example, the remaining capacity of the battery 1496 and voltage, current, or temperature thereof while the battery 1496 is charged. The battery 1496 may include, for example, a rechargeable battery or a solar battery.

The indicator 1497 may display a specific state of the electronic device 1401 or a part (e.g., the AP 1410) thereof, for example, a booting state, a message state, or a charging state, and the like. The motor 1498 may convert an electric signal into mechanical vibration and may generate vibration or a haptic effect, and the like. Though not shown, the electronic device 1401 may include a processing unit (e.g., a GPU) for supporting a mobile TV. The processing unit for supporting the mobile TV may process media data according to standards, for example, a digital multimedia broadcasting (DMB) standard, a digital video broadcasting (DVB) standard, or a media flow standard, and the like.

Each of the above-mentioned elements of the electronic device according to various embodiments of the present disclosure may be configured with one or more components, and names of the corresponding elements may be changed according to the type of the electronic device. The electronic device according to various embodiments of the present disclosure may include at least one of the above-mentioned elements, some elements may be omitted from the electronic device, or other additional elements may be further included in the electronic device. Also, some of the elements of the electronic device according to various embodiments of the present disclosure may be combined with each other to form one entity, thereby making it possible to perform the functions of the corresponding elements in the same manner as before the combination.

The terminology "module" used herein may mean, for example, a unit including one of hardware, software, and firmware or two or more combinations thereof. The terminology "module" may be interchangeably used with, for example, terminologies "unit", "logic", "logical block", "component", or "circuit", and the like. The "module" may be a minimum unit of an integrated component or a part thereof. The "module" may be a minimum unit performing one or more functions or a part thereof. The "module" may be mechanically or electronically implemented. For example, the "module" may include at least one of an application-specific IC (ASIC) chip, field-programmable gate arrays (FPGAs), or a programmable-logic device, which is well known or will be developed in the future, for performing certain operations.

According to various embodiments of the present disclosure, at least a part of the electronic device (e.g., modules or the functions) or the method (e.g., operations) may be implemented with, for example, instructions stored in a computer-readable storage media which has a program module. When the instructions are executed by a processor, one or more processors may perform functions corresponding to the instructions. The computer-readable storage media may be, for example, the memory.

The computer-readable storage media may include a hard disc, a floppy disk, magnetic media (e.g., a magnetic tape), optical media (e.g., a compact disc ROM (CD-ROM), a DVD), magneto-optical media (e.g., a floptical disk), and a hardware device (e.g., a ROM, a RAM, or a flash memory, and the like), and the like. Also, the program instructions may include not only mechanical codes compiled by a compiler but also high-level language codes which may be executed by a computer using an interpreter and the like. The above-mentioned hardware device may be configured to operate as one or more software modules to perform operations according to various embodiments of the present disclosure, and vice versa.

Modules or program modules according to various embodiments of the present disclosure may include at least one or more of the above-mentioned components, some of the above-mentioned components may be omitted, or other additional components may be further included. Operations executed by modules, program modules, or other elements according to various embodiments of the present disclosure may be executed by a successive method, a parallel method, a repeated method, or a heuristic method. Also, some operations may be executed in a different order or may be omitted, and other operations may be added.

According to various embodiments of the present disclosure, the electronic device may enhance visibility of information and the degree of understanding of information according to displaying information in a more dynamic way and displaying information to be adaptive to a situation.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device comprising:
a memory configured to store at least one object;
a display configured to output a screen associated with the at least one object; and
at least one processor configured to functionally connect with the memory and the display,
wherein the at least one processor is further configured to control to:
obtain sensing information related to a human body from the memory when current sensing information is collected,
calculate an entire measurement range based on statistics of the obtained sensing information,
change a maximum range value and a minimum range value representing the calculated entire measurement range from a default maximum range value and a default minimum range value, and
display a first object corresponding to the changed maximum range value and minimum range value and a second object corresponding to the collected current sensing information on the first object, and
wherein the at least one processor is further configured to adjust a display change speed of a numeric value of the maximum range value and the minimum range value such that a change of a numeric value which reaches the minimum range value and a change of a numeric value which reaches the maximum range value are completed at a same time.

2. The electronic device of claim 1, wherein the at least one processor is further configured to control to display a third object, corresponding to a representative value obtained from the sensing information, on the first object or the second object.

3. The electronic device of claim 2,
wherein the at least one processor is further configured to control to display the representative value, corresponding to the third object, on a region adjacent to a position where the third object is displayed, or
wherein the at least one processor is further configured to control the modifying or displaying of the second object relative to a position to display the third object.

4. The electronic device of claim 2, wherein the at least one processor is further configured to adjust a display speed of a modified region of the second object such that a time when the second object is modified and displayed is identical relative to the third object.

5. The electronic device of claim 2,
wherein the at least one processor is further configured to control to display a range of values of sensing information associated with the first object on a region adjacent to the first object,
wherein the at least one processor is further configured to control to display a range of values of sensing information associated with the second object on a region adjacent to the second object, and
wherein the at least one processor is further configured to control to display the representative value, according to the accumulated sensing information, with a numeral and gradually change the numeric value from the numeral to become the range of values.

6. The electronic device of claim 5, wherein the at least one processor is further configured to:
change the numeric value, and
display a start value of the range of values and an end value of the range of values.

7. The electronic device of claim 1,
wherein the at least one processor is further configured to collect physical characteristic information associated with a state of the electronic device or a state of the human body which provides the sensing information and modify a display state of at least one of the first object, the second object, or a third object according to the physical characteristic information, or
wherein the at least one processor is further configured to:
convert the sensing information into a constant numeric value, and
modify and display the second object while mapping the numeric value to the second object.

8. A method of displaying information in an electronic device, the method comprising:
obtaining sensing information related to a human body from a memory when current sensing information is collected;
calculating an entire measurement range based on statistics of the obtained sensing information;

changing a maximum range value and a minimum range value representing the calculated entire measurement range from a default maximum range value and a default minimum range value, and displaying a first object corresponding to the changed maximum range value and minimum range value and a second object corresponding to the collected current sensing information on the first object wherein the displaying comprises adjusting a display change speed of a numeric value of the maximum range value and the minimum range value such that a change of a numeric value which reaches the minimum range value and a change of a numeric value which reaches the maximum range value are completed at a same time.

9. The method of claim 8, further comprising:

displaying a third object, corresponding to a representative value obtained from the sensing information, on the first object or the second object.

10. The method of claim 9, further comprising:

displaying the representative value, corresponding to the third object, on a region adjacent to a position where the third object is displayed.

11. The method of claim 9, wherein the displaying of the third object comprises:

modifying and displaying the second object relative to a position to display the third object; or adjusting and displaying a display speed of a modified region of the second object such that a time when the second object is modified and displayed is identical relative to the third object.

12. The method of claim 9, further comprising:

at least one of displaying a first range of values of sensing information associated with the first object on a region adjacent to the first object or displaying a second range of values of sensing information associated with the second object on a region adjacent to the second object.

13. The method of claim 12, further comprising:

gradually changing a numeric value of a numeral indicating the representative value to become the second range value; or adjusting and displaying a display change speed of a numeric value such that a change of a start numeric value corresponding to a start value of the second range of values and a change of an end numeric value corresponding to an end value of the second range of values are completed at a same time.

14. The method of claim 9, further comprising:

collecting physical characteristic information associated with a state of the electronic device or a state of the human body which provides the sensing information; and modifying a display state of at least one of the first object, the second object, and a third object according to the physical characteristic information.

15. An electronic device comprising:

a local-area communication module configured to establish a local-area communication channel with an external electronic device;

a memory configured to store sensing information received through the local-area communication module and at least one object to be output based on the sensing information; and a processor configured to control to:

change, based on the sensing information, a maximum range value and a minimum range value of a first range of values from a default maximum range value and a default minimum range value, display a first object corresponding to the first range of values in connection with the stored sensing information, and control to output at least one of a second object, corresponding to a calculated second range of values corresponding to the measured sensing information associated with automatically determined current measurement state information, which is displayed in a form which is gradually changed from a position in the first object or a third object corresponding to a single value in the first range of values, wherein the at least one processor is further configured to adjust a display change speed of a numeric value of the maximum range value and the minimum range value such that a change of a numeric value which reaches the minimum range value and a change of a numeric value which reaches the maximum range value are completed at a same time.

* * * * *